(12) United States Patent
Shelton, IV et al.

(10) Patent No.: US 7,434,715 B2
(45) Date of Patent: *Oct. 14, 2008

(54) SURGICAL STAPLING INSTRUMENT HAVING MULTISTROKE FIRING WITH OPENING LOCKOUT

(75) Inventors: Frederick E. Shelton, IV, Hillsboro, OH (US); Jeffrey S. Swayze, Hamilton, OH (US); Douglas B. Hoffman, Harrison, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1040 days.

This patent is subject to a terminal disclaimer.

(21) Appl. No.: 10/674,236

(22) Filed: Sep. 29, 2003

(65) Prior Publication Data

US 2005/0070925 A1   Mar. 31, 2005

(51) Int. Cl.
*A61B 17/10* (2006.01)
(52) U.S. Cl. .................. 227/175.2; 227/19; 227/175.1; 227/178.1
(58) Field of Classification Search ............. 227/175.1, 227/178.1, 179.1, 175.2, 19, 182.1, 180.1
See application file for complete search history.

(56) References Cited

U.S. PATENT DOCUMENTS

| | | | |
|---|---|---|---|
| 448,194 | A | 3/1891 | Balbin |
| 804,229 | A | 11/1905 | Hutchinson |
| 1,944,166 | A | 1/1934 | Stratman |
| 2,883,984 | A | 4/1959 | Candido, Jr. et al. |
| 3,269,630 | A | 8/1966 | Fleisher |
| 3,661,187 | A | 5/1972 | Caveney et al. |
| 3,837,555 | A | 9/1974 | Green |
| 3,949,924 | A | 4/1976 | Green |
| 3,955,581 | A | 5/1976 | Spasiano et al. |
| 4,154,239 | A | 5/1979 | Turley |
| 4,276,878 | A | 7/1981 | Storz |
| 4,304,236 | A * | 12/1981 | Conta et al. ............... 227/179.1 |
| 4,580,712 | A | 4/1986 | Green |
| 4,589,870 | A | 5/1986 | Citrin et al. |
| RE32,214 | E | 7/1986 | Schramm |
| 4,606,343 | A | 8/1986 | Conta et al. |
| 4,664,305 | A | 5/1987 | Blake, III et al. |
| 4,671,278 | A | 6/1987 | Chin |
| 4,869,415 | A | 9/1989 | Fox |

(Continued)

FOREIGN PATENT DOCUMENTS

EP    0 070 230 A1    7/1982

(Continued)

*Primary Examiner*—Brian D Nash
(74) *Attorney, Agent, or Firm*—Frost Brown Todd LLC

(57) ABSTRACT

A surgical stapling and severing instrument particularly suited to endoscopic procedures incorporates a handle that produces separate closing and firing motions to actuate an end effector. In particular, the handle produces multiple firing strokes in order to reduce the required amount of force required to fire (i.e., staple and sever) the end effector. A linked transmission reduces the required handle longitudinal length, yet achieves a rigid, strong configuration when straightened for firing. A traction biased firing mechanism avoids binding in driving this straightened linked rack in cooperation with an anti-backup mechanism, with a lockout mechanism that prevents releasing the closure trigger during firing. Furthermore, an external indicator gives feedback to the surgeon as to how far firing has progressed, as well as providing a manual retraction capability.

7 Claims, 20 Drawing Sheets

U.S. PATENT DOCUMENTS

| | | | |
|---|---|---|---|
| 4,976,686 A | 12/1990 | Ball et al. | |
| 5,005,749 A * | 4/1991 | Aranyi | 227/19 |
| 5,040,715 A | 8/1991 | Green et al. | |
| 5,104,025 A * | 4/1992 | Main et al. | 227/175.1 |
| 5,137,198 A * | 8/1992 | Nobis et al. | 227/175.3 |
| 5,271,543 A * | 12/1993 | Grant et al. | 227/179.1 |
| 5,307,976 A | 5/1994 | Olson et al. | |
| 5,314,424 A | 5/1994 | Nicholas | |
| 5,318,221 A * | 6/1994 | Green et al. | 227/178.1 |
| 5,376,095 A | 12/1994 | Ortiz | |
| 5,413,267 A | 5/1995 | Solyntjes et al. | |
| 5,467,911 A | 11/1995 | Tsuruta et al. | |
| 5,482,197 A | 1/1996 | Green et al. | |
| 5,509,596 A | 4/1996 | Green et al. | |
| 5,535,935 A * | 7/1996 | Vidal et al. | 227/175.2 |
| 5,573,541 A | 11/1996 | Green et al. | |
| 5,579,978 A | 12/1996 | Green et al. | |
| 5,630,539 A * | 5/1997 | Plyley et al. | 227/175.1 |
| 5,706,997 A | 1/1998 | Green et al. | |
| 5,706,998 A | 1/1998 | Plyley et al. | |
| 5,728,108 A | 3/1998 | Griffiths et al. | |
| 5,730,740 A | 3/1998 | Wales et al. | |
| 5,735,445 A | 4/1998 | Vidal et al. | |
| 5,735,874 A | 4/1998 | Measamer et al. | |
| 5,762,255 A * | 6/1998 | Chrisman et al. | 227/175.2 |
| 5,762,256 A | 6/1998 | Mastri et al. | |
| 5,782,396 A | 7/1998 | Mastri et al. | |
| 5,826,776 A | 10/1998 | Schulze et al. | |
| 5,855,311 A | 1/1999 | Hamblin et al. | |
| 5,865,361 A | 2/1999 | Milliman et al. | |
| 5,893,506 A | 4/1999 | Powell | |
| 5,894,979 A | 4/1999 | Powell | |
| 5,976,160 A | 11/1999 | Crainich | |
| 6,010,054 A | 1/2000 | Johnson et al. | |
| 6,032,849 A | 3/2000 | Mastri et al. | |
| 6,079,606 A | 6/2000 | Milliman et al. | |
| 6,120,526 A | 9/2000 | Daley | |
| 6,241,139 B1 | 6/2001 | Milliman et al. | |
| 6,330,965 B1 | 12/2001 | Milliman et al. | |
| 7,083,075 B2 * | 8/2006 | Swayze et al. | 227/176.1 |
| 7,303,108 B2 * | 12/2007 | Shelton, IV | 227/179.1 |
| 2002/0117533 A1 | 8/2002 | Milliman et al. | |

FOREIGN PATENT DOCUMENTS

| WO | WO 99/15086 | 4/1999 |
|---|---|---|

\* cited by examiner

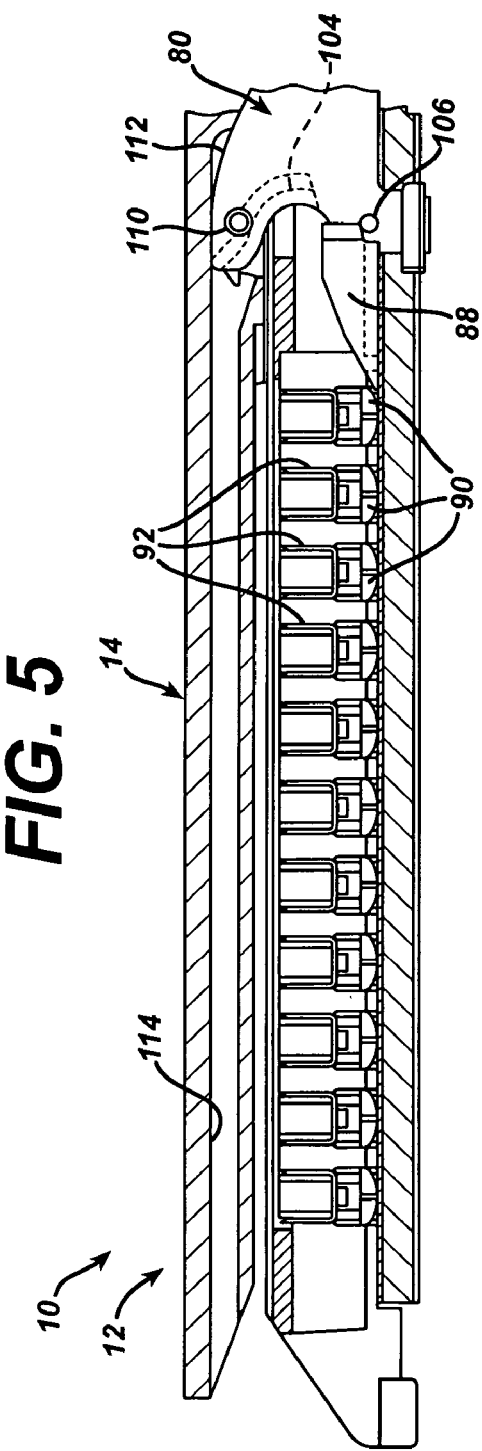
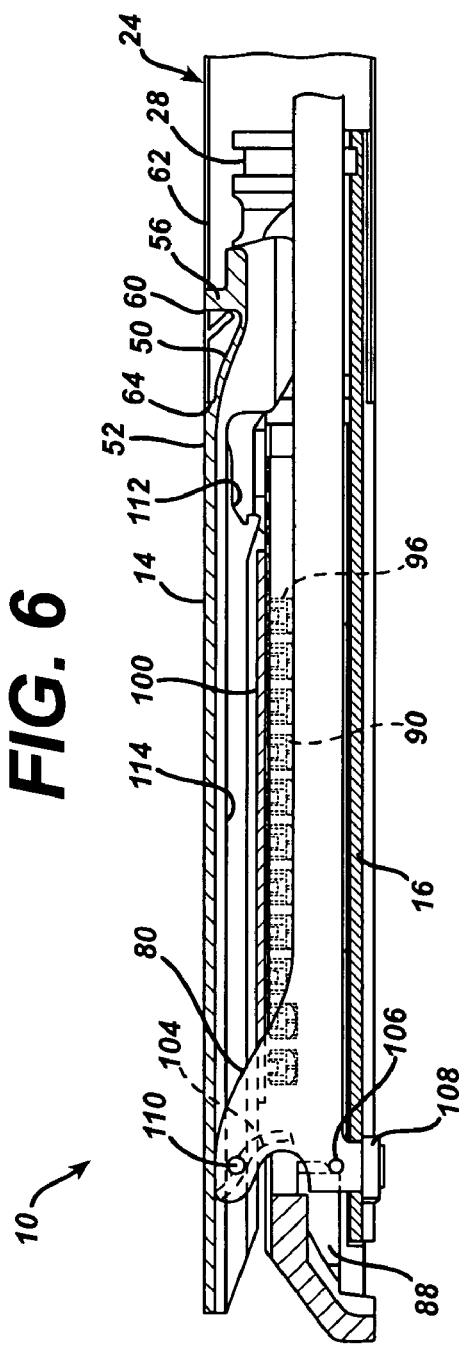

SURGICAL STAPLING INSTRUMENT HAVING MULTISTROKE FIRING WITH OPENING LOCKOUT

CROSS REFERENCE TO RELATED APPLICATIONS

The present application is related to four commonly-owned applications filed on even date herewith, the disclosure of each is hereby incorporated by reference in their entirety, these four applications being respectively entitled:

"SURGICAL STAPLING INSTRUMENT WITH MULTISTROKE FIRING INCORPORATING AN ANTI-BACKUP MECHANISM, U.S. Pat. No. 6,959,852, to Frederick E. Shelton, Mike Setser;

"SURGICAL STAPLING INSTRUMENT INCORPORATING A FIRING MECHANISM HAVING A LINKED RACK TRANSMISSION", U.S. Pat. No. 6,905,057, to Jeffrey S. Swayze, Frederick E. Shelton IV;

"SURGICAL STAPLING INSTRUMENT HAVING MULTISTROKE FIRING INCORPORATING A TRACTION-BIASED RATCHETING MECHANISM, U.S. Pat. No. 7,000,819, to Jeffrey S. Swayze, Frederick E. Shelton IV; and "SURGICAL STAPLING INSTRUMENT INCORPORATING A MULTISTROKE FIRING POSITION INDICATOR AND RETRACTION MECHANISM, Ser. No. 10/674,026, pending, to Jeffrey S. Swayze, Frederick E. Shelton IV.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments that accomplish firing with multiple strokes of a trigger.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which advantageously provides distinct closing and firing actions. Thereby, a clinician is able to close the jaw members upon tissue to position the tissue prior to firing. Once the clinician has determined that the jaw members are properly gripping tissue, the clinician can then fire the surgical stapler with a single firing stroke, thereby severing and stapling the tissue. The simultaneous severing and stapling avoids complications that may arise when performing such actions sequentially with different surgical tools that respectively only sever or staple.

One specific advantage of being able to close upon tissue before firing is that the clinician is able to verify via an endoscope that desired location for the cut has been achieved, including a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Generally, a single closing stroke followed by a single firing stroke is a convenient and efficient way to perform severing and stapling. However, in some instances, it would be desirable for multiple firing strokes to be required. For example, surgeons are able to select from a range of jaw sizes with a corresponding length of staple cartridge for the desired length of cut. Longer staple cartridges require a longer firing stroke. Thus, a hand-squeezed trigger to effect the firing is required to exert a larger force for these longer staple cartridges in order to sever more tissue and drive more staples as compared to a shorter staple cartridge. It would be desirable for the amount of force to be lower and comparable to shorter cartridges so as not to exceed the hand strength of some surgeons. In addition, some surgeons not familiar with the larger staple cartridges may become concerned that binding or other malfunction has occurred when an unexpectedly higher force is required.

One approach to lower the required force for a firing stroke is a ratcheting mechanism that allows a firing trigger to be stroked multiple times, as described in U.S. Pat. Nos. 5,762,256 and 6,330,965. These known surgical stapling instruments with multiple-stroke firing mechanisms do not have the advantages of a separate closure and firing action. Moreover, the ratcheting mechanism relies upon a toothed rack and driving pawl to achieve the ratcheting motion, with the length of a handle encompassing these components thus increased to accommodate the toothed rack. This increased length is inconvenient given the close confines and increasing amount of equipment associated with a surgical procedure.

While having a multiple stroke firing mechanism advantageously mitigates required force to fire, it may increase the likelihood of partial firing due to human error. In closed procedures, the surgeon may be unable to determine when the firing mechanism has gone full travel, achieving complete severing and stapling. In addition, the surgeon may be unfamiliar with the number of firing strokes required to achieve this full firing travel, especially if using staple cartridges of various sizes.

Some end effectors include a firing lockout that prevents opening prior to retracting the firing bar; however, in some instances such a lockout is not a complete prevention of inadvertent opening of the instrument. For instance, there may be sufficient clearances and deflection in the components between the end effector and the closure release mechanism of the handle to release or partially release the clamped closure handle when the stapling and severing operation is not complete.

Consequently, a significant need exists for a surgical stapling instrument with a multiple stroke firing mechanism that prevents inadvertent opening of the instrument before full firing travel thereof.

BRIEF SUMMARY OF THE INVENTION

The invention overcomes the above-noted and other deficiencies of the prior art by providing a surgical stapling instrument that has the advantages of separate opening and firing, yet includes an opening lockout in the handle to prevent an attempt to open a clamped implement portion when partially fired.

In one aspect of the invention, a surgical instrument has an elongate implement portion that responds a firing motion and a closure motion. A closing mechanism closes and opens the implement portion. With the implement portion closed, a firing mechanism produces the firing motion between an unfired position and a fully fired position to fire the implement portion. A closing release mechanism locks the closing mechanism when the implement portion is in the fully closed position and responds to an operator command to unlock the closing mechanism only when the firing mechanism is in an unfired position. Thereby, malfunction or an improper surgical operation are avoided by allowing an inadvertent attempt to open the implement portion of the surgical instrument when the partially fired. Consequently, some undesirable situations are avoided such as a surgical stapling and severing procedure when tissue is only partially stapled and severed.

In another aspect of the invention, a surgical instrument has an elongate implement portion that responds to a firing motion and a closure motion. A handle portion that is connected to the elongate implement portion performs a number of functions for the implement portion. In particular, a firing mechanism operably produces the firing motion between an unfired position and a fully fired position. An indicator member responds to the firing mechanism being in the unfired position by positioning a lockout surface in an unlocked position. A closure trigger produces the closure motion, moveable between an open position and a closed position, and is lockable at the closed position. An unlocking control is moveable from an unactuated to an actuated position to unlock the closure trigger when the lockout surface of the indicator member is in the unlocked position. Thereby, the condition of the firing mechanism (i.e., unfired) is an enabling condition to safely allow the unlocking of a clamped implement portion.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 5 depicts a left side elevation view in section of the end effector of FIG. 3 of the surgical instrument of FIG. 1, the section generally taken along lines 5-5 of FIG. 3 to expose portions of a staple cartridge but also depicting the firing bar along the longitudinal centerline.

FIG. 6 depicts a left side elevation view in section of the end effector of FIG. 5 after the firing bar has fully fired.

DETAILED DESCRIPTION OF THE INVENTION

Figure 1:
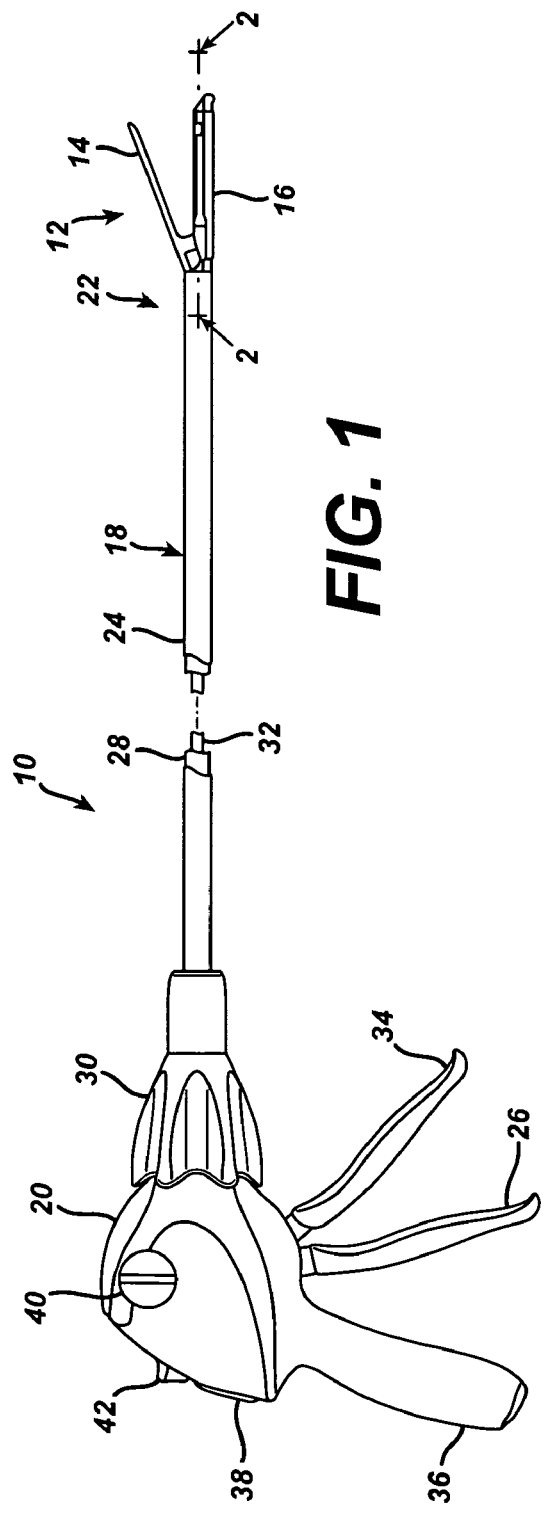
FIG. 1 is a right side elevation view of a surgical stapling and severing instrument in an open (start) condition, with a shaft partially cutaway to expose a closure tube and firing rod.
Figure 2:
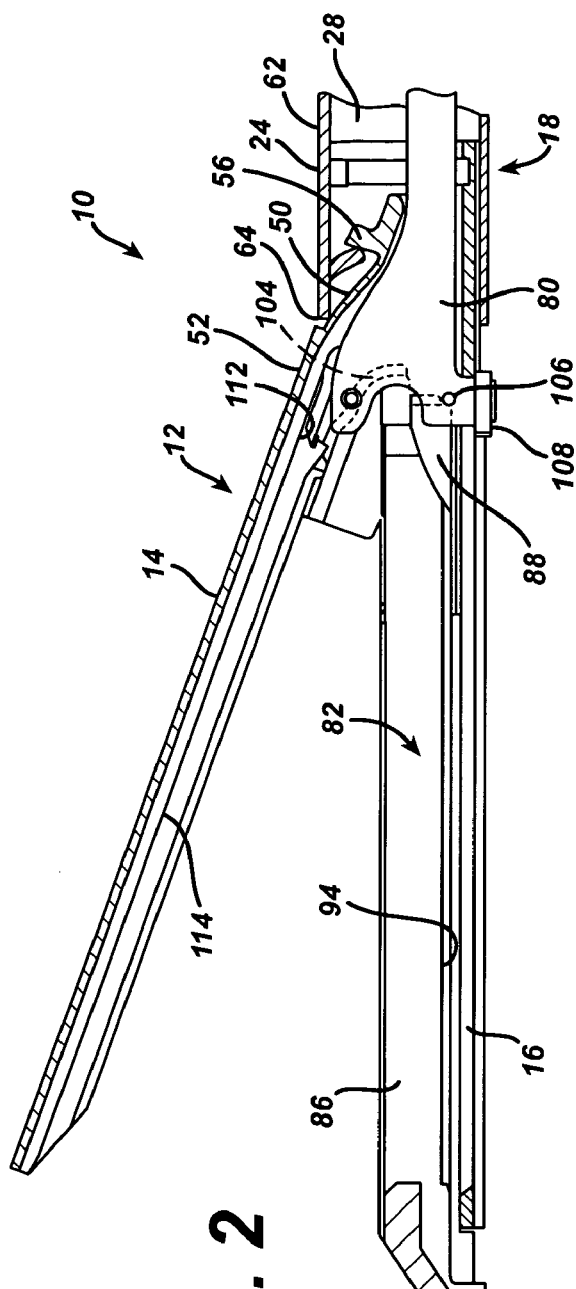
FIG. 2 is a left side elevation view taken along line 2-2 in longitudinal cross section of an end effector at a distal portion of the surgical stapling instrument of FIG. 1.

Turning to the Drawings, wherein like numerals denote like components throughout the several views, FIGS. 1 and 2 depict a surgical stapling and severing instrument 10 that is capable of practicing the unique benefits of the present invention. The surgical stapling and severing instrument 10 incorporates an end effector 12 having an anvil 14 pivotally attached to an elongate channel 16, forming opposing jaws for clamping tissue to be severed and stapled. The end effector 12 is coupled by a shaft 18 to a handle 20. An implement portion 22, formed by the end effector 12 and shaft 18, is advantageously sized for insertion through a trocar or small laparoscopic opening to perform an endoscopic surgical procedure while being controlled by a surgeon grasping the handle 20. The handle 20 advantageously includes features that allow separate closure motion of the end effector 12 from firing, as well as enabling multiple firing strokes to effect firing (i.e., severing and stapling) of the end effector 12 while indicating the degree of firing to the surgeon.

To these ends, a closure tube 24 of the shaft 18 is coupled between a closure trigger 26 and the anvil 14 to cause closure of the end effector 12. Within the closure tube 24, a frame 28 is coupled between the elongate channel 16 and the handle 20 to longitudinally position and support the end effector 12. A rotation knob 30 is coupled with the frame 28, and both elements are rotatably coupled to the handle 20 with respect to a rotational movement about a longitudinal axis of the shaft 18. Thus, the surgeon can rotate the end effector 12 by turning the rotation knob 30. The closure tube 24 is also rotated by the rotation knob 30 but retains a degree of longitudinal movement relative thereto to cause the closure of the end effector 12. Within the frame 28, a firing rod 32 is positioned for longitudinal movement and coupled between the anvil 14 of the end effector 12 and a multiple-stroke firing trigger 34. The closure trigger 26 is distal to a pistol grip 36 of the handle 20 with the firing trigger 34 distal to both the pistol grip 36 and closure trigger 26.

In endoscopic operation, once the implement portion 22 is inserted into a patient to access a surgical site, a surgeon refers to an endoscopic or other diagnostic imaging device to position tissue between the anvil 14 and elongate channel 16. Grasping the closure trigger 26 and pistol grip 36, the surgeon may repeatedly grasp and position the tissue. Once satisfied as to the location of the tissue relative to the end effector 12 and the amount of tissue therein, the surgeon depresses the closure trigger 26 fully toward the pistol grip 36, clamping the tissue in the end effector 12 and locking the closure trigger 26 in this clamped (closed) position. If not satisfied with this position, the surgeon may release the closure trigger 26 by depressing a closure release button 38 and thereafter repeat the procedure to clamp tissue.

If clamping is correct, the surgeon may proceed with firing the surgical stapling and severing instrument 10. Specifically, the surgeon grasps the firing trigger 34 and pistol grip 36, depressing the firing trigger 34 a predetermined number of times. The number of firing strokes necessary is ergonomically determined based on a maximum hand size, maximum amount of force to be imparted to the instrument during each firing stroke, and the longitudinal distance and force needed to be transferred through the firing rod 32 to the end effector 12 during firing. As will be appreciated in the discussion below, individual surgeons may choose to cycle the firing trigger 34 a different angular range of motion, and thus increase or decrease the number of firing strokes, yet the handle 20 still effects firing without binding.

During these strokes, the surgeon may reference an indicator, depicted as an indicating retraction knob 40, that positionally rotates in response to the multiple firing strokes. Additionally, the position of the retraction knob may confirm that full firing has occurred when encountering resistance to further cycling of the firing trigger 34. It should be appreciated that various indicia and instructions may be added to the handle 20 to enhance the indication provided by the rotation of the indicating retraction knob 40. Upon full travel of the firing rod 32 and when the firing trigger 34 is released, the handle 20 automatically retracts the firing rod 32. Alternatively, the surgeon, with knowledge that the instrument 10 has not fully fired as depicted by the indicating retraction knob 40, may depress an anti-backup release button 42 and release the firing trigger 34. Both of these actions allow the handle 20 to automatically retract the firing rod 32.

It will be appreciated that the terms "proximal" and "distal" are used herein with reference to a clinician gripping a handle of an instrument. Thus, the end effector 12 is distal with respect to the more proximal handle 20. It will be further appreciated that for convenience and clarity, spatial terms such as "vertical" and "horizontal" are used herein with respect to the drawings. However, surgical instruments are used in many orientations and positions, and these terms are not intended to be limiting and absolute.

The present invention is being discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

E-Beam End Effector.

Figure 3:
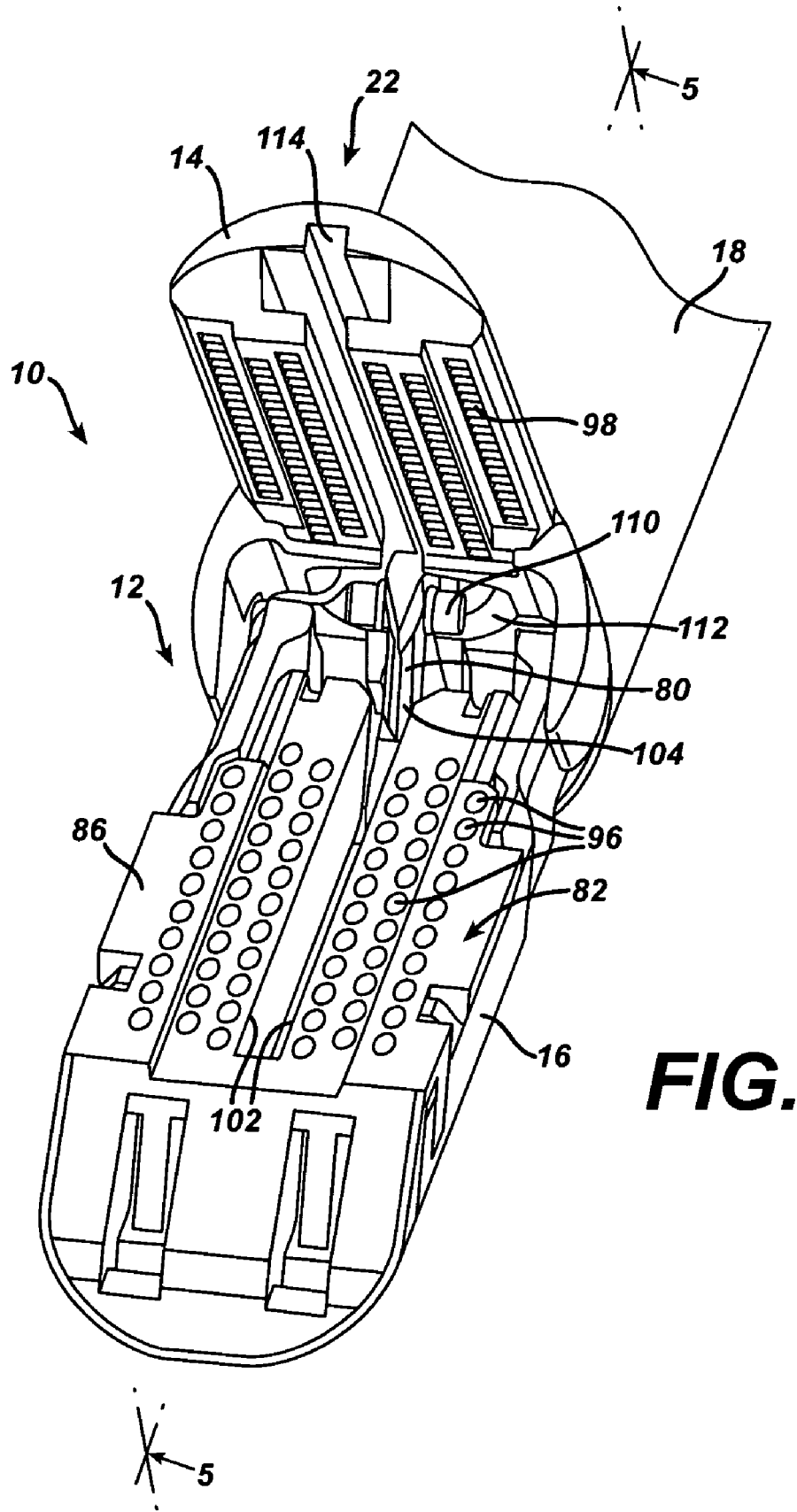
FIG. 3 is a front perspective view of the end effector of FIG. 2.
Figure 4:
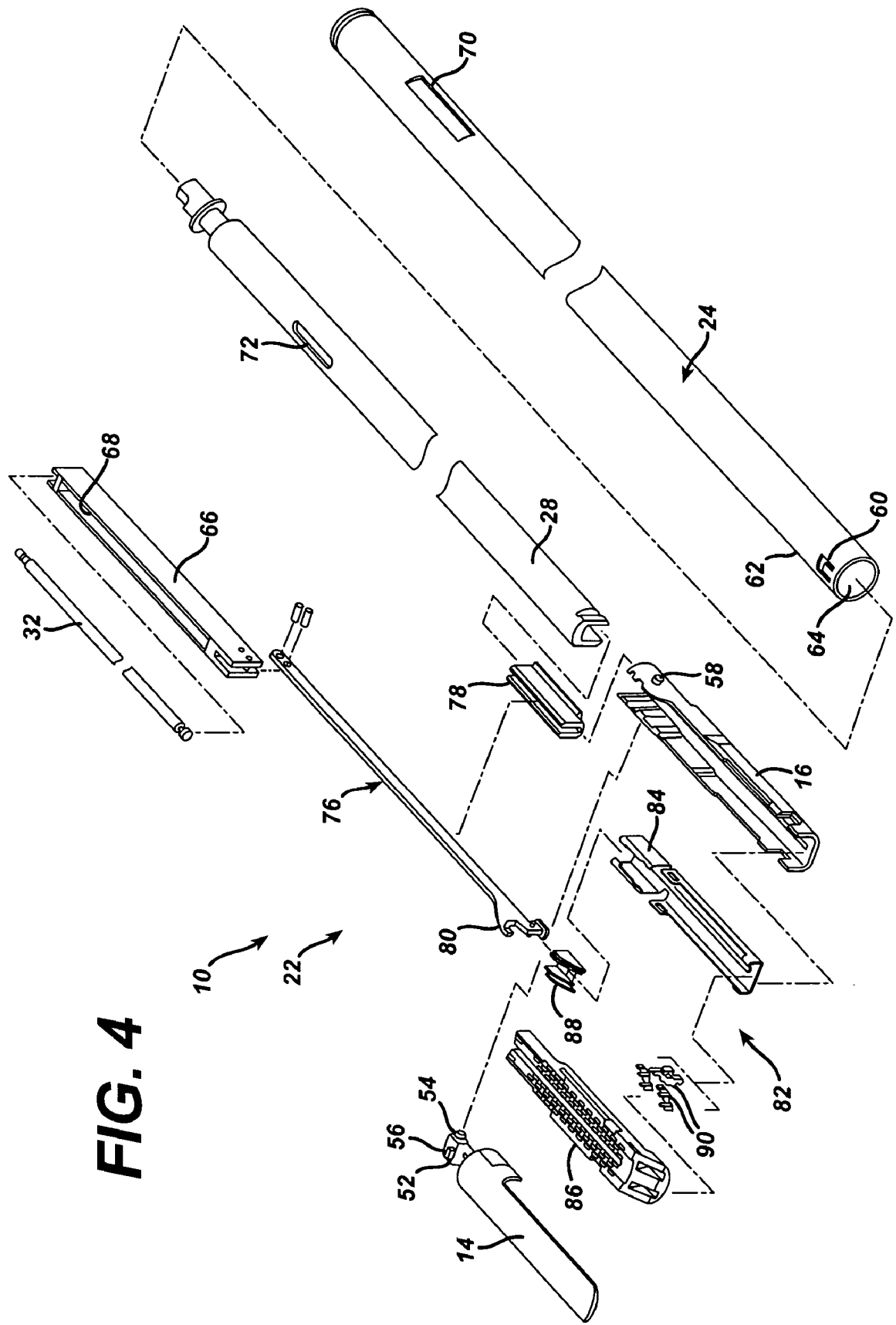
FIG. 4 is a perspective, exploded view of an implement portion of the surgical stapling and severing instrument of FIG. 1.

The advantages of a handle 20 capable of providing multiple-stroke firing motion has application to a number of instruments, with one such end effector 12 being depicted in FIGS. 2-6. The end effector 12 responds to the closure motion from the handle 20 (not depicted in FIGS. 2-6) first by including an anvil face 50 (FIGS. 2, 4, 6) connecting to an anvil proximal end 52 that includes a pair of laterally projecting anvil pivot pins 54 that are distal to a vertically projecting anvil feature 56 (FIG. 4). The anvil pivot pins 54 translate within kidney shaped openings 58 in the elongate channel 16 to open and close anvil 14 relative to elongate channel 16. The anvil feature 56 engages a bent tab 59 extending inwardly in tab aperture 60 on a distal end 62 of the closure tube 24, the latter distally terminating in a distal edge 64 that pushes against the anvil face 50. Thus, when the closure tube 24 moves proximally from its the open position, the bent tab 59 of the closure tube 24 draws the anvil feature 56 proximally, and the anvil pivot pins 54 follow the kidney shaped openings 58 of the channel 16 causing the anvil 14 to simultaneously translate proximally and rotate upward to the open position. When the closure tube 24 moves distally, the tab aperture 60 releases from the anvil feature 56 and the distal edge 64 pushes on the anvil face 50, closing the anvil 14.

With continued reference to FIG. 4, the implement portion 22 also includes components that respond to the firing motion of the firing rod 32. In particular, the firing rod 32 rotatably engages a firing trough member 66 having a longitudinal recess 68. Firing trough member 66 moves longitudinally within frame 28 in direct response to longitudinal motion of firing rod 32. A longitudinal slot 70 in the closure tube 24 operably couples with the rotation knob 30 (not shown in FIGS. 2-6). The length of the longitudinal slot 70 in the closure tube 24 is sufficiently long as to allow relative longitudinal motion with the rotation knob 30 to accomplish firing and closure motions respectively.

The distal end of the frame trough member 66 is attached to a proximal end of a firing bar 76 that moves with the frame 28, including a guide 78 therein, to distally project an E-beam 80 into the end effector 12. The end effector 12 includes a staple cartridge 82 that is actuated by the E-beam 80. The staple cartridge 82 has a tray 84 that holds a staple cartridge body 86, a wedge sled driver 88, staple drivers 90 and staples 92. It will be appreciated that the wedge sled driver 88 longitudinally moves within a recess 94 located between a cartridge tray 84 and the cartridge body 86. The wedge sled driver 88 presents camming surfaces that contact and lift the staple drivers 90 upward, driving the staples 92 up from staple apertures 96 into contact with staple forming grooves 98 of the anvil 14, creating formed "B" shaped staples, such as depicted at 100 of FIG. 6. With particular reference to FIG. 3, the staple cartridge body 86 further includes a proximally open, vertical slot 102 for passage of the E-beam 80. Cutting surface 104 is provided along a distal end of E-beam 80 to cut tissue after it is stapled.

In FIGS. 2, 5, 6, respectively, the end effector 12 is depicted in a sequence of open (i.e., start) condition, clamped and unfired condition, and fully fired condition. Features of the E-beam 80 that facilitate firing of the end effector 12, in particular, are depicted. In FIG. 2, the wedge sled driver 88 is in its fully proximally position, indicating an unfired staple cartridge 82. A middle pin 106 is aligned to enter the firing recess 94 in the staple cartridge 82, for distally driving the wedge sled driver 88. A bottom pin or cap 108 of the E-beam 82 slides along a bottom surface of the elongate channel 16, thus the middle and bottom pins 106, 108 slidingly engage the elongate channel 16. In the open and unfired state of FIG. 2, a top pin 110 of the E-beam 80 has entered and is residing within an anvil pocket 112 of the anvil 14, and thus does not impede repeated opening and closing of the anvil 14.

In FIG. 5, the end effector 12 is depicted as clamped and ready to fire. The top pin 110 of the E-beam 80 is aligned with an anvil slot 114 in the anvil 14 distal to and communicating with the anvil pocket 112. In FIG. 6, the E-beam 80 has been fully fired, with the upper pin 110 translating down the anvil slot 114, affirmatively spacing the anvil 14 from the elongate channel 16 as the cutting surface 104 severs clamped tissue. Simultaneously, the middle pin 106 has actuated the staple cartridge 82 as previously described. Thereafter, the E-beam 80 is retracted prior to opening the end effector 12 and replacing the staple cartridge 82 for an additional operation.

The illustrative end effector 12 is described in greater detail in five co-pending and commonly-owned U.S. patent applications, the disclosure of each being hereby incorporated by reference in their entirety: (1) "SURGICAL STAPLING INSTRUMENT HAVING A SINGLE LOCKOUT MECHANISM FOR PREVENTION OF FIRING", Ser. No. 10/441,424, to Frederick E. Shelton, Mike Setser, Bruce Weisenburgh, filed 20 Jun. 2003; (2) "SURGICAL STAPLING INSTRUMENT HAVING SEPARATE DISTINCT CLOSING AND FIRING SYSTEMS", Ser. No. 10/441,632, to Frederick E. Shelton, Mike Setser, Brian J. Hemmelgarn, filed 20 Jun. 2003; (3) "SURGICAL STAPLING INSTRUMENT HAVING A SPENT CARTRIDGE LOCKOUT", Ser. No. 10/441,565, to Frederick E. Shelton, Mike Setser, Bruce Weisenburgh, filed 20 Jun. 2003; (4) "SURGICAL STAPLING INSTRUMENT HAVING A FIRING LOCKOUT FOR AN UNCLOSED ANVIL", Ser. No. 10/441,580, to Frederick E. Shelton, Mike Setser, Bruce Weisenburgh, filed 20 Jun. 2003; and (5) "SURGICAL STAPLING INSTRUMENT INCORPORATING AN E-BEAM FIRING MECHANISM", Ser. No. 10/443,617, to Frederick E. Shelton, Mike Setser, Bruce Weisenburgh, filed 20 Jun. 2003.

It should be appreciated that although a nonarticulating shaft 18 is illustrated herein, applications of the present invention may include instruments capable of articulation, such as described in five co-pending and commonly owned U.S. patent applications, the disclosure of each being hereby incorporated by reference in their entirety: (1) "SURGICAL INSTRUMENT INCORPORATING AN ARTICULATION MECHANISM HAVING ROTATION ABOUT THE LONGITUDINAL AXIS", Ser. No. 10/615,973, to Frederick E. Shelton, Brian J. Hemmelgarn, Jeff Swayze, Kenneth S. Wales, filed 9 Jul. 2003; (2) "SURGICAL STAPLING INSTRUMENT INCORPORATING AN ARTICULATION JOINT FOR A FIRING BAR TRACK", Ser. No. 10/615,962, to Brian J. Hemmelgarn, filed 9 Jul. 2003; (3) "A SURGICAL INSTRUMENT WITH A LATERAL-MOVING ARTICULATION CONTROL", Ser. No. 10/615972, to Jeff Swayze, filed 9 Jul. 2003; (4) "SURGICAL STAPLING INSTRUMENT INCORPORATING A TAPERED FIRING BAR FOR INCREASED FLEXIBILITY AROUND THE ARTICULATION JOINT", Ser. No. 10/615,974, to Frederick E. Shelton, Mike Setser, Bruce Weisenburgh, filed 9 Jul. 2003; and (5) "SURGICAL STAPLING INSTRUMENT HAVING ARTICULATION JOINT SUPPORT PLATES FOR SUPPORTING A FIRING BAR", Ser. No. 10/615,971, to Jeff Swayze, Joseph Charles Hueil, filed 9 Jul. 2003.

It should further be appreciated that the linked rack 200 further may enhance a compact design for the handle 20 by progressing at least partially into the shaft 18 of the implement portion 22 as well as around a corner and into a pistol grip 36 of the handle. Moreover, instead of communicating the firing force to a firing rod 32, a linked rack consistent with aspects of the invention may travel farther toward the end effector 12 to include an articulation mechanism. A pivotal connection between links may thus enhance the ability of the instrument to articulate.

Multi-stroke Firing Handle.

Figure 7:
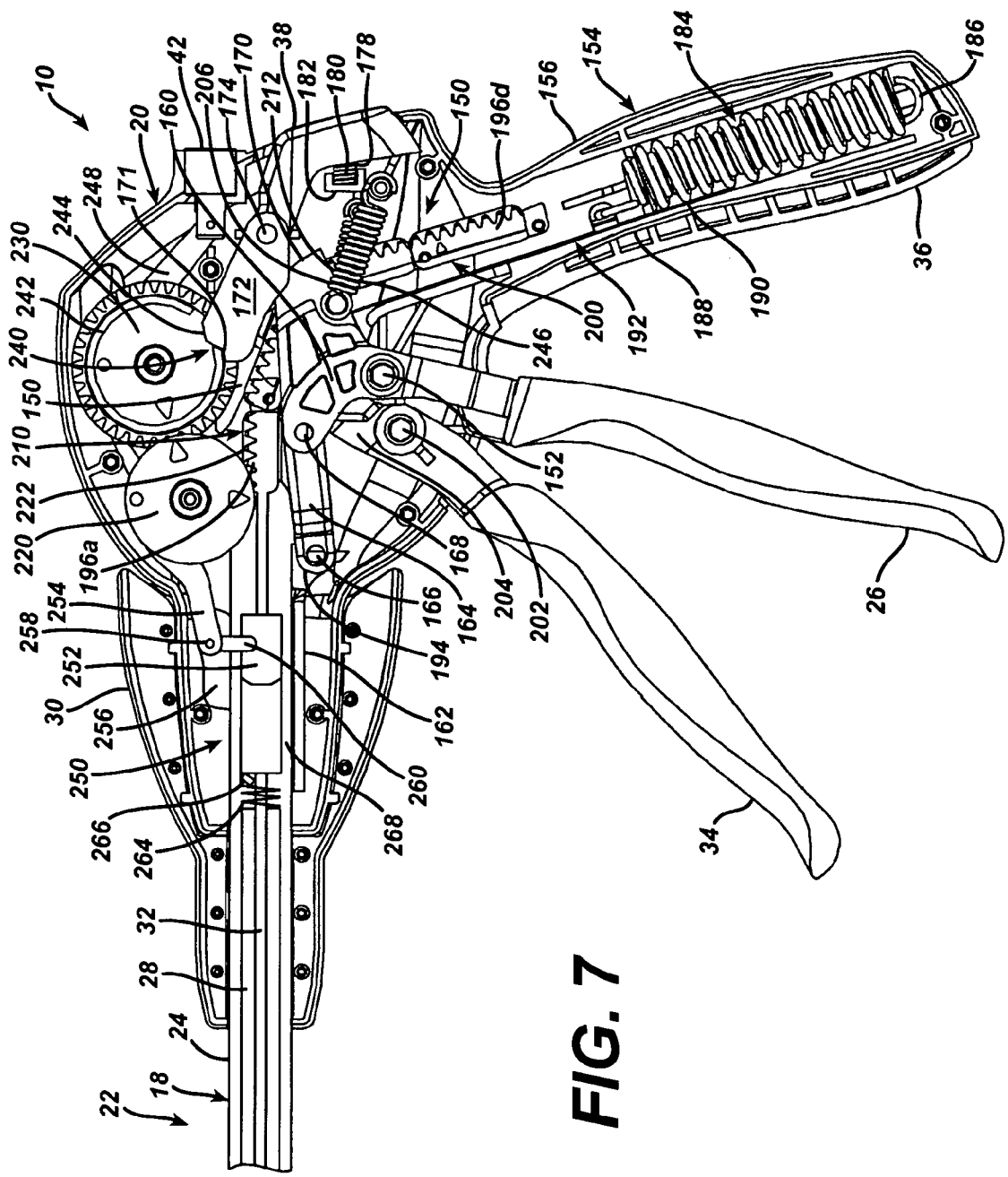
FIG. 7 is a left side elevation view of the handle of the surgical stapling and severing instrument of FIG. 1 with a left handle housing removed.
Figure 8:
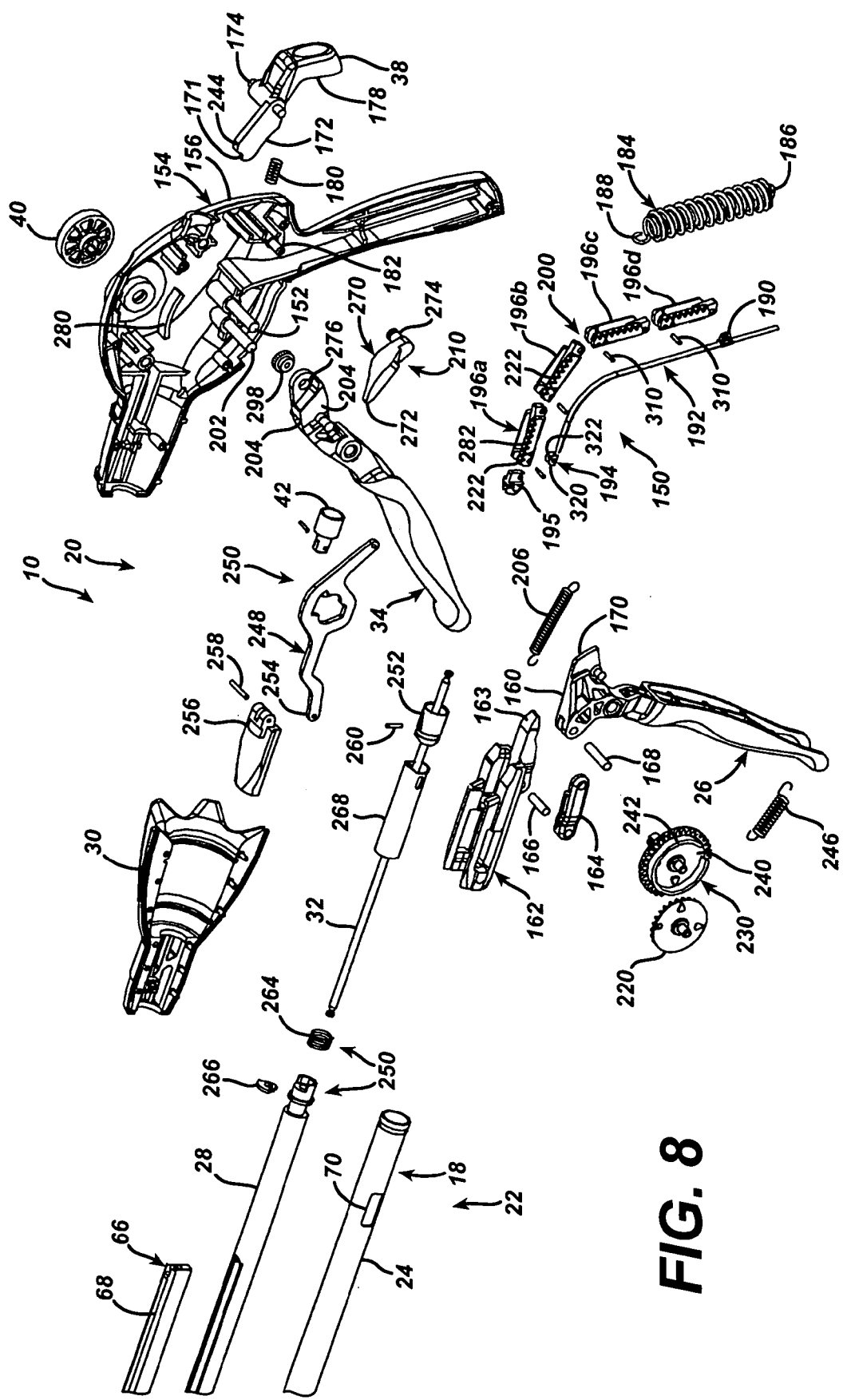
FIG. 8 is a perspective, exploded view of the handle of FIG. 7.

In FIGS. 7-8, the handle 20 of the surgical stapling and severing instrument 10 is shown in greater detail, illustrating a linked transmission firing mechanism 150 that provides features such as increased strength, reduced handle size, minimized binding, etc.

Closure of the end effector 12 (not shown in FIGS. 7-8) is caused by depressing the closure trigger 26 toward the pistol grip 36 of handle 20. The closure trigger 26 pivots about a closure trigger pin 152 that is coupled to a handle housing 154 composed of right and left half shells 156, 158, causing an upper portion 160 of the closure trigger 26 to move forward. The closure tube 24 receives this closure movement via a closure yoke 162 that is pinned to a closure link 164 and to the upper portion 160 of the closure trigger 26 respectively by a closure yoke pin 166 and a closure link pin 168.

In the fully open position of FIG. 7, the upper portion 160 of the closure trigger 26 contacts and holds a locking arm 172 of the pivoting closure release button 38 in the position shown. When the closure trigger 26 reaches its fully depressed position, the closure trigger 26 releases the locking arm 172 and an abutting surface 170 rotates into engagement with a distal rightward notch 171 of the pivoting locking arm 172, holding the closure trigger 26 in this clamped or closed position. A proximal end of the locking arm 172 pivots about a lateral pivotal connection 174 with the housing 154 to expose the closure release button 38. An intermediate, distal side 178 of the closure release button 38 is urged proximally by a compression spring 180, which is compressed between a housing structure 182 and closure release button 38. The result is that the closure release button 38 urges the locking arm 172 counterclockwise (when viewed from the left) into locking contact with the abutting surface 170 of closure trigger 26, which prevents unclamping of closure trigger 26 when the linked transmission firing system 150 is in an unretracted condition, as described in greater detail below.

With the closure trigger 26 retracted fully depressed, the firing trigger 34 is unlocked and may be depressed toward the pistol grip 36 multiple times to effect firing of the end effector 12. As depicted, the linked transmission firing mechanism 150, is initially retracted, urged to remain in this position by a combination tension/compression spring 184 that is constrained within the pistol grip 36 of the handle 20, with its nonmoving end 186 connected to the housing 154 and a moving end 188 connected to a downwardly flexed and proximal, retracted end 190 of a steel band 192.

A distally-disposed end 194 of the steel band 192 is attached to a link coupling 195 for structural loading and front link 196a of a plurality of links 196a-196d that form a linked rack 200. Linked rack 200 is flexible yet has distal links that form a straight rigid rack assembly that may transfer a significant firing force through the firing rod 32 in the implement portion 22, yet readily retract into the pistol grip 36 to minimize the longitudinal length of the handle 20.

It should be appreciated that a dual tension/compression spring 184 increases the amount of firing travel available while essentially reducing the minimum length by half over a single spring.

The firing trigger 34 pivots about a firing trigger pin 202 that is connected to the housing 154. An upper portion 204 of the firing trigger 34 moves distally about the firing trigger pin 202 as the firing trigger 34 is depressed towards pistol grip 36, stretching a proximally placed firing trigger tension spring 206 proximally connected between the upper portion 204 of the firing trigger 34 and the housing 154. The upper portion 204 of the firing trigger 34 engages the linked rack 200 during each firing trigger depression by a traction biasing mechanism 210 that also disengages when the firing trigger 34 is released. Firing trigger tension spring 206 urges the firing trigger 34 distally when released and disengages the traction biasing mechanism 210.

As the firing mechanism 150 actuates, an idler gear 220 is rotated counterclockwise (as viewed from the left side) by engagement with a toothed upper surface 222 of the linked rack 200. This rotation is coupled to an indicator gear 230, which thus rotates clockwise in response to the idler gear 220. Both the idler gear 220 and indicator gear 230 are rotatably connected to the housing 154. The gear relationship between the linked rack 200, idler gear 220 and indicator gear 230 may be advantageously selected so that the toothed upper surface 222 has tooth dimensions that are suitably strong and that the indicator gear 230 makes no more than one revolution during the full firing travel of the firing mechanism 150.

As described in greater detail below, the indicator gear 230 performs at least four functions. First, when the linked rack 200 is fully retracted and both triggers 26, 34 are open as shown in FIG. 7, an opening 240 in a circular ridge 242 on the left side of the indicator gear 230 is presented to an upper surface 244 of the locking arm 172. Locking arm 172 is biased into the opening 240 by contact with the closure trigger 26, which in turn is urged to the open position by a closure tension spring 246. Closure trigger tension spring 246 is connected proximally to the upper portion 160 of the closure trigger 26 and the handle housing 154, and thus has energy stored during closing of the closure trigger 26 that urges the closure trigger 26 distally to its unclosed position.

A second function of the indicator gear 230 is that it is connected to the indicating retraction knob 40 externally disposed on the handle 20. Thus, the indicator gear 230 communicates the relative position of the firing mechanism 150 to the indicating retraction knob 40 so that the surgeon has a visual indication of how many strokes of the firing trigger 34 are required to complete firing.

A third function of the indicator gear 230 is to longitudinally and to angularly move an anti-backup release lever 248 of an anti-backup mechanism 250 as the surgical stapling and severing instrument 10 is operated. During the firing strokes, proximal movement of anti-backup release lever 248 by indicator gear 230 activates a one-way clutch mechanism or anti-backup 250 (FIGS. 15-16) that allows distal movement of firing bar 32 and prevents proximal motion of firing bar 32. This movement also extends the anti-backup release button 42 from the proximal end of the housing 154 for the operator to actuate should the need arise for the firing mechanism to be retracted during the firing strokes. After completion of the firing strokes, the indicator gear 230 reverses direction of rotation as the firing mechanism 150 retracts. The reversed rotation deactivates the anti-backup 250, withdraws the anti-backup release button 42 into the handle 20, and rotates the anti-backup release lever 248 laterally (FIG. 19) to allow continued reverse rotation of the indicator gear 230.

A fourth function of the indicator gear 230 is to receive a manual rotation from the indicating retraction knob 40 (clockwise in the depiction of FIG. 7) to retract the firing mechanism 150 with anti-backup mechanism 250 is unlocked, thereby overcoming any binding in the firing mechanism 150 that is not readily overcome by the combination tension/compression spring 184. This manual retraction may be employed after a partial firing of the firing mechanism 150 that would otherwise be prevented by the anti-backup mechanism 250 by depression of the anti-backup release button 42, which laterally moves the anti-backup release lever 248.

Anti-backup mechanism 250 consists of an operator accessable anti-backup release lever 248 operably coupled at the proximal end to anti-backup release lever 42 and at the distal end to an anti-backup yoke 256. In particular, a distal end 254 of the anti-backup release lever 248 is engaged to the anti-backup yoke 256 by an anti-backup yoke pin 258. The anti-backup yoke 256 moves longitudinally to impart a rotation to an anti-backup cam slot tube 252 that is longitudinally constrained by the housing 154 and that encompasses the firing rod 32 distally to the connection of the firing rod 32 to the front link 196a of the linked rack 200. The anti-backup yoke 256 communicates the longitudinal movement from the anti-backup release lever 248 via a cam slot tube pin 260 to the anti-backup cam slot tube 252. That is, longitudinal movement of cam slot tube pin 260 in an angled slot in the anti-backup cam slot tube 252 rotates the tube 252.

Trapped between a proximal end of the frame 28 and the anti-backup cam slot tube 252 respectively are an anti-backup compression spring 264, an anti-backup plate 266, and an anti-backup cam tube 268. As depicted, distal movement of the firing rod 32 causes the anti-backup plate 266 to pivot top to the rear, presenting an increased frictional contact to the firing rod 32 that resists proximal movement of the firing rod 32.

This anti-backup plate 266 pivots in a manner similar to that of a screen door lock that holds open a screen door when the anti-backup cam slot tube 252 is spaced away from the anti-backup cam tube 268. Specifically, the anti-backup compression spring 264 is able to act upon a top surface of the plate 266 to tip the plate 266 to its locked position. Rotation of the anti-backup cam slot tube 252 causes a distal camming movement of the anti-backup cam tube 268 forcing the top of the plate 266 distally, overcoming the force from the anti-backup compression spring 264, thus positioning the anti-backup plate 266 in an unlocked position that allows proximal retraction of the firing rod 32.

Figure 9:
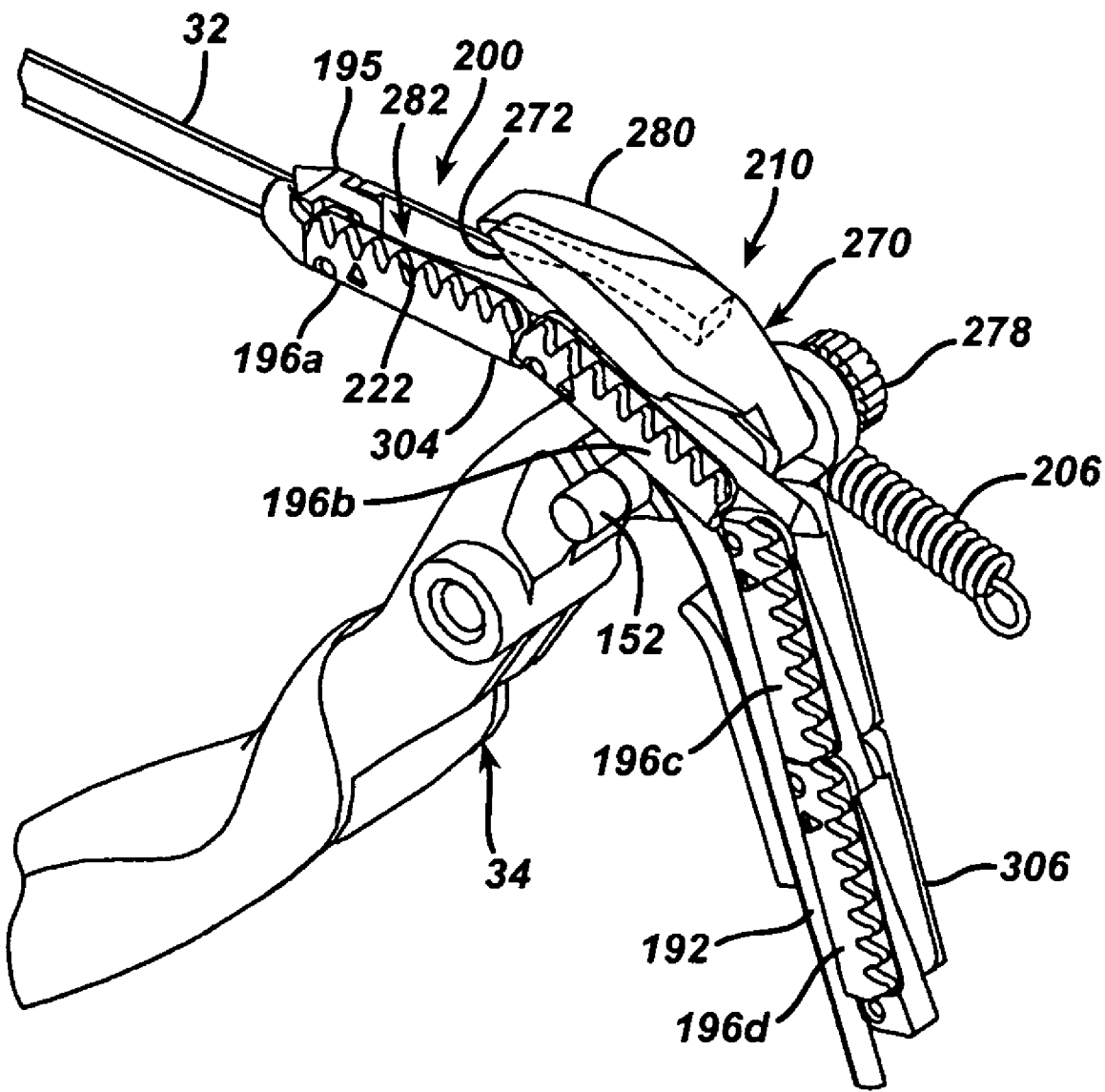
FIG. 9 is a perspective view from an elevated, aft, left vantage point of the linked transmission firing mechanism of the handle of FIG. 7.
Figure 10:
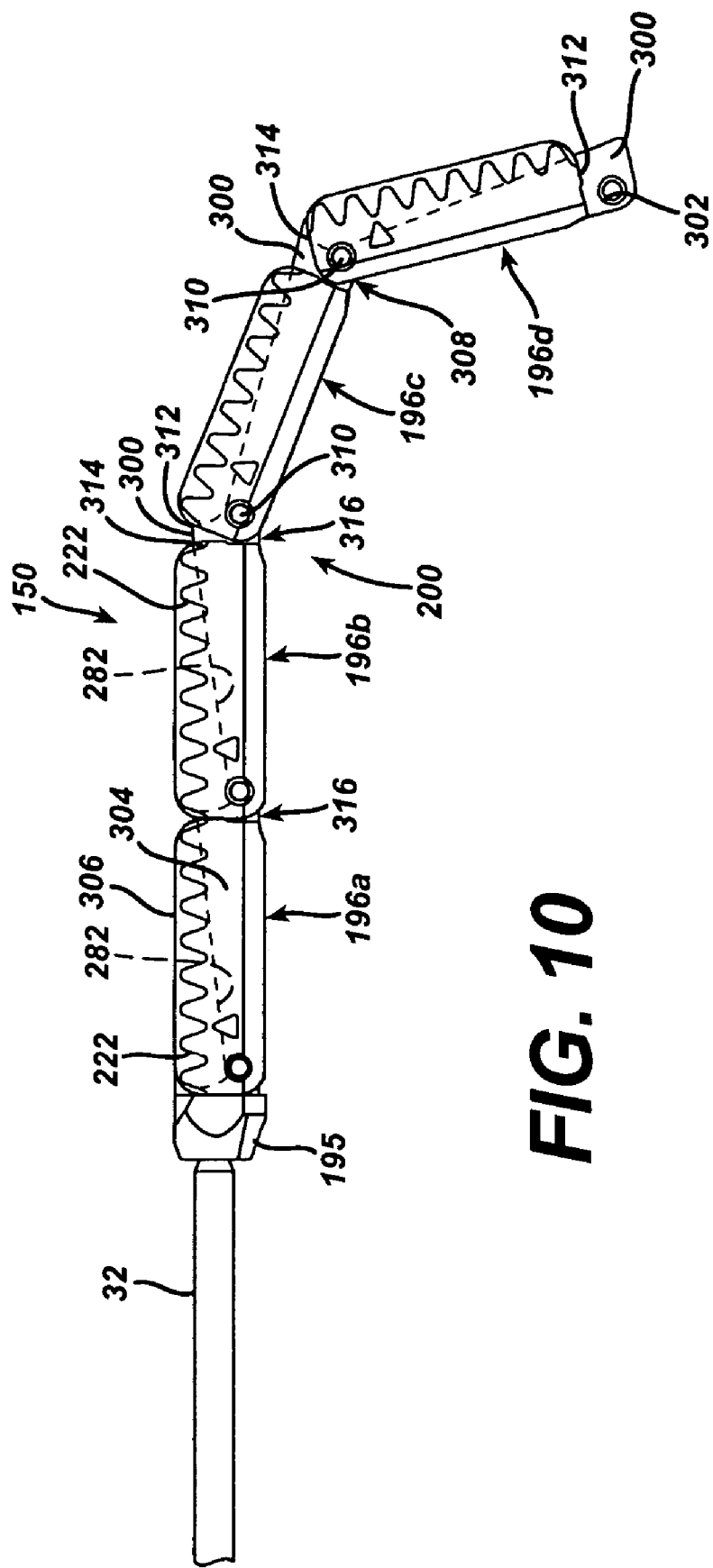
FIG. 10 is a detail left side elevation view of the linked rack of the firing mechanism of FIG. 9.

With particular reference to FIGS. 8-10, the traction biasing mechanism 210 is depicted as being composed of a pawl 270 that has a distally projecting narrow tip 272 and a rightwardly projecting lateral pin 274 at its proximal end that is rotatably inserted through a hole 276 in the upper portion 204 of the firing trigger 34. On the right side of the firing trigger 34, the lateral pin 274 receives a biasing member, depicted as biasing wheel 278. As the firing trigger 34 translates fore and aft, the biasing wheel 278 traverses an arc proximate to the right half shell 156 of the handle housing 154, overrunning at its distal portion of travel a biasing ramp 280 integrally formed in the right half shell 156. The biasing wheel 278 may advantageously be formed from a resilient, frictional material that induces a counterclockwise rotation (when viewed from the left) into the lateral pin 274 of the pawl 270, thus traction biasing the distally projecting narrow tip 272 downward into a ramped central track 282 of the nearest link 196*a-d* to engage the linked rack 200. As the firing trigger 34 is released, the biasing wheel 278 thus tractionally biases the pawl 270 in the opposite direction, raising the narrow tip 272 from the ramped central track 282 of the linked rack 200. To ensure disengagement of the tip 272 under high load conditions and at nearly full distal travel of the pawl 270, the narrow tip 272 ramps up onto a proximally and upwardly facing beveled surface 284 on the closure yoke 162 to disengage the narrow tip 272 from the ramped central track 282. If the firing trigger 34 is released at any point other than full closure, the biasing wheel 278 is used to lift the narrow tip 272 from the ramped central track 282. Whereas a biasing wheel 278 is depicted, it should be appreciated that the shape of the biasing member or wheel 278 is illustrative and may be varied to accommodate a variety of shapes that use friction or traction to engage or disengage the firing of the end effector.

Linked Rack.

With particular reference to FIG. 10, the linked rack 200 is depicted in greater detail to illustrate a number of advantages. Each link 196*a-d* is pinned to adjacent links 196*a-d* for downward, proximal rotation into the pistol grip 36. Although bendable in this direction, the linked rack 200 forms a rigid configuration when against a columnar loading, especially a loading that would other urge the distal links 196*a-d* to bend upwardly. In particular, each link 196*a-d* proximally terminates in a male extension 300 having lateral through hole 302 on a lower portion thereof. A left side 304 of each link 196*a-d* includes the toothed upper surface 222 and a right side 306 parallels the left side 304 defining between them the ramped central track 282 that terminates in the male extension 300.

The proximal portion of the central track 282 terminates before the right and left sides 304, 306, forming a device 308 for receiving a male extension 300 from a leading link 196*a-d*, which is hingedly attached by a pivot pin 310. Each leading link 196*a-d* has a flat 312 at the proximal end that is generally perpendicular to the direction of columnar loading from the firing rod 32. Each trailing link 196*a-d* has a contact surface 314 at the distal end that is also generally perpendicular to the direction of columnar loading. The lateral through hole 302 is spaced away sufficient so that a notch 316 is formed between lower portions of adjacent flat 312 and contact surface 314 to provide clearance for downward pivoting of the trailing link 196*a-d* relative to the leading link 196*a-d*. Yet, the upper portions of the adjacent flat 312 and contact surface 314 are registered for abutment as the leading and trailing links 196*a-d* are longitudinally aligned, thereby resisting further upward deflection. As shown, when adjacent links 196*a-d* are horizontal, the holes 302 and pins 310 are located below the line of action of the firing rod 32. When loads are applied to the firing trigger 34, the traction biasing mechanism 210 applies a pushing load along the line of action and biases consecutive horizontal links 196*a-d* together. Thus, imparting a line of action of a firing force above the pivot pins 310 maintains any leading links 196*a-d* in a rigid, straight configuration. The ramped central track 282 of a trailing link 196*b-d* directs the distally projecting narrow tip 272 of the pawl 270 into engagement with the male extension 300 of the leading link 196*a-c*.

The front link 196*a* is distally attached to the link coupling 195 that includes features that couple to the proximal end of the firing rod 32 as well as including a male extension 300 and flat 312 similar to the links 196*a-d*, with sufficient spacing to receive therebetween tabs 320, 322 (FIG. 8) of the distally-disposed end 194 of the steel band 192, the tabs 320, 322 attached by the same pivot pin 310 that attaches the front link 196*a* to the link coupling 195. Application of the retraction force at this force advantageously reduces frictional forces by applying the force along the longitudinal axis of the firing rod 32 and straight portion of the linked rack 200.

Having a toothed upper surface 222 on the left side 304 that is distinct from the ramped central track 282 advantageously allows a nonbinding, strong engagement between the pawl 270 and the linked rack 200, even if the firing trigger 34 has been stroked with varying ranges of motion. Meanwhile the toothed upper surface 222 provides a continuous engagement with the idler gear 220 for the advantages described above.

It should be appreciated that although a pinned clevis connection between links 196*a-d* has been advantageously depicted, a resilient or flexible connection may be used. In addition, four links 196*a-d* are depicted, but various numbers and lengths of links may be selected depending on firing travel, radius of curvature, etc.

Traction-Biasing Mechanism.

In FIGS. 11-14, the linked transmission firing mechanism 150 is depicted in a sequence that illustrates how the traction biasing mechanism 210 (i.e., pawl 270, biasing wheel 278, and biasing ramp 280) affirmatively respond to the direction of travel of the firing trigger 34. Moreover, since the biasing wheel 278 makes a frictional contact with the biasing ramp 280, the biasing wheel 278 slides when full disengagement or engagement movement of the pawl 270 is achieved.

Figure 11:
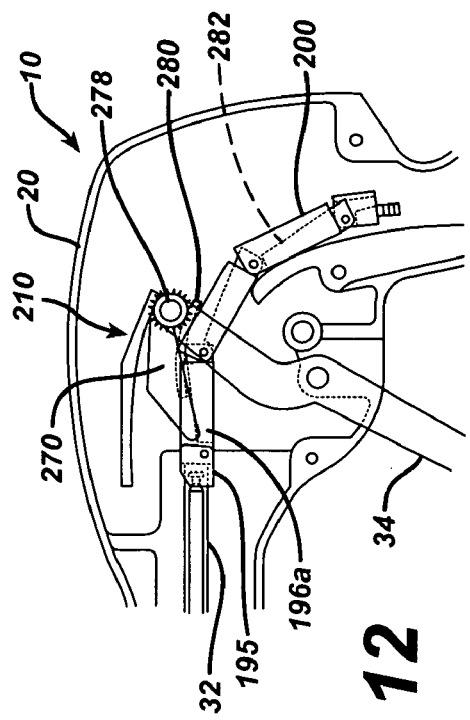
FIGS. 11-14 are left side elevation views in cross section generally along the longitudinal axis of the ramped central track of the linked rack and the pawl of the firing mechanism, and additionally showing the firing trigger, biasing wheel and ramp of the traction biasing mechanism, depicting a sequence during a firing stroke.
Figure 12:
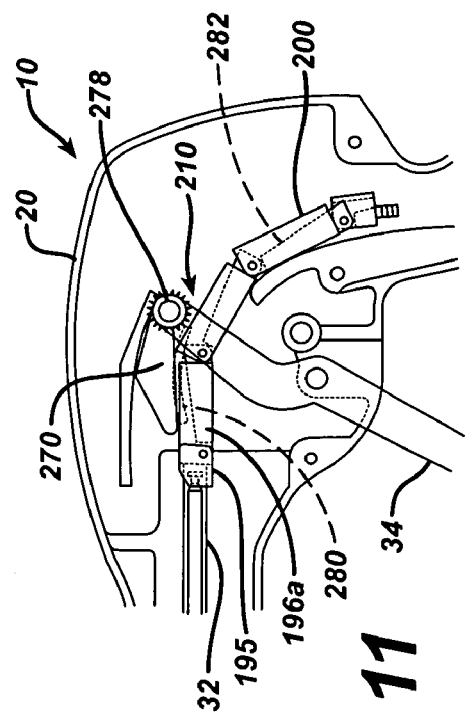
Figure 13:
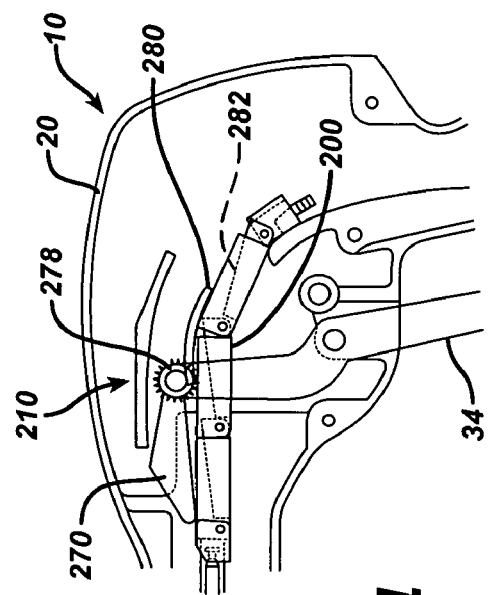

In FIG. 11, the firing trigger 34 has been partially depressed to where the traction biasing mechanism 210 begins to initiate engagement of the firing trigger 34 movement to the linked rack 200. In particular, the biasing wheel 278 has contacted the proximal end of the biasing ramp 280, and thus begins to rotate counterclockwise, as viewed from the left, imparting this rotation to the pawl 270, which is initially disengaged from the linked rack 200. In FIG. 12, the firing mechanism 150 has advanced a distance sufficient for the pawl 270 to have fully rotated into engagement with the ramped central track 282 of the first link 196*a*, abutting the link coupling 195 and thereby transferring a firing motion into the firing rod 32. In FIG. 13, the firing trigger 34 and overall firing mechanism 150 has continued to a nearly full travel position, during which movement the biasing wheel 278 has slid along the biasing ramp 280. At the end of the firing stroke, the farside lower edge of the pawl 270 (FIG. 8) contacts the proximally and upwardly facing beveled surface 284 of the closure yoke 162 and lifts the pawl 270 from engagement with a link 196, allowing the linked rack 200 to retract.

Figure 14:
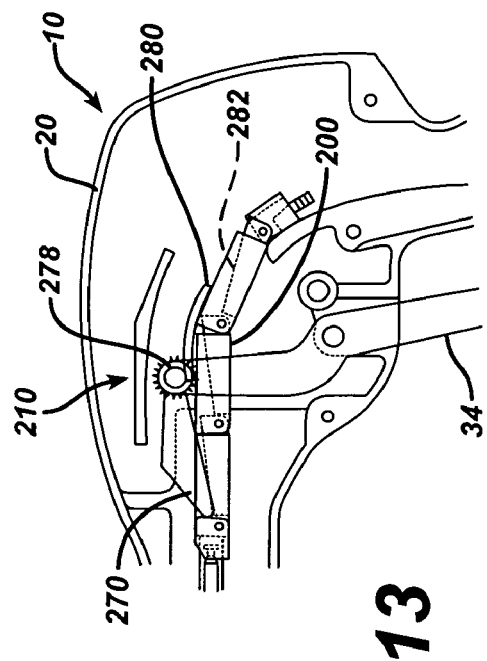

In FIG. 14, the firing trigger 34 has been released sufficient for the biasing wheel 278 to gain traction proximally on the biasing ramp 280, causing a clockwise rotation, when viewed from the left, and raising the pawl 270. Given the proximally directed slope of the ramped central track 282 of the linked rack 200, the firing mechanism 150 is not obstructed in being moved proximally in preparation for either another firing stroke or for a retraction cycle.

It should be appreciated that the traction biasing mechanism 210 may be implemented in an instrument that performs at least a single stroke.

Anti-backup Mechanism.

Figure 15:
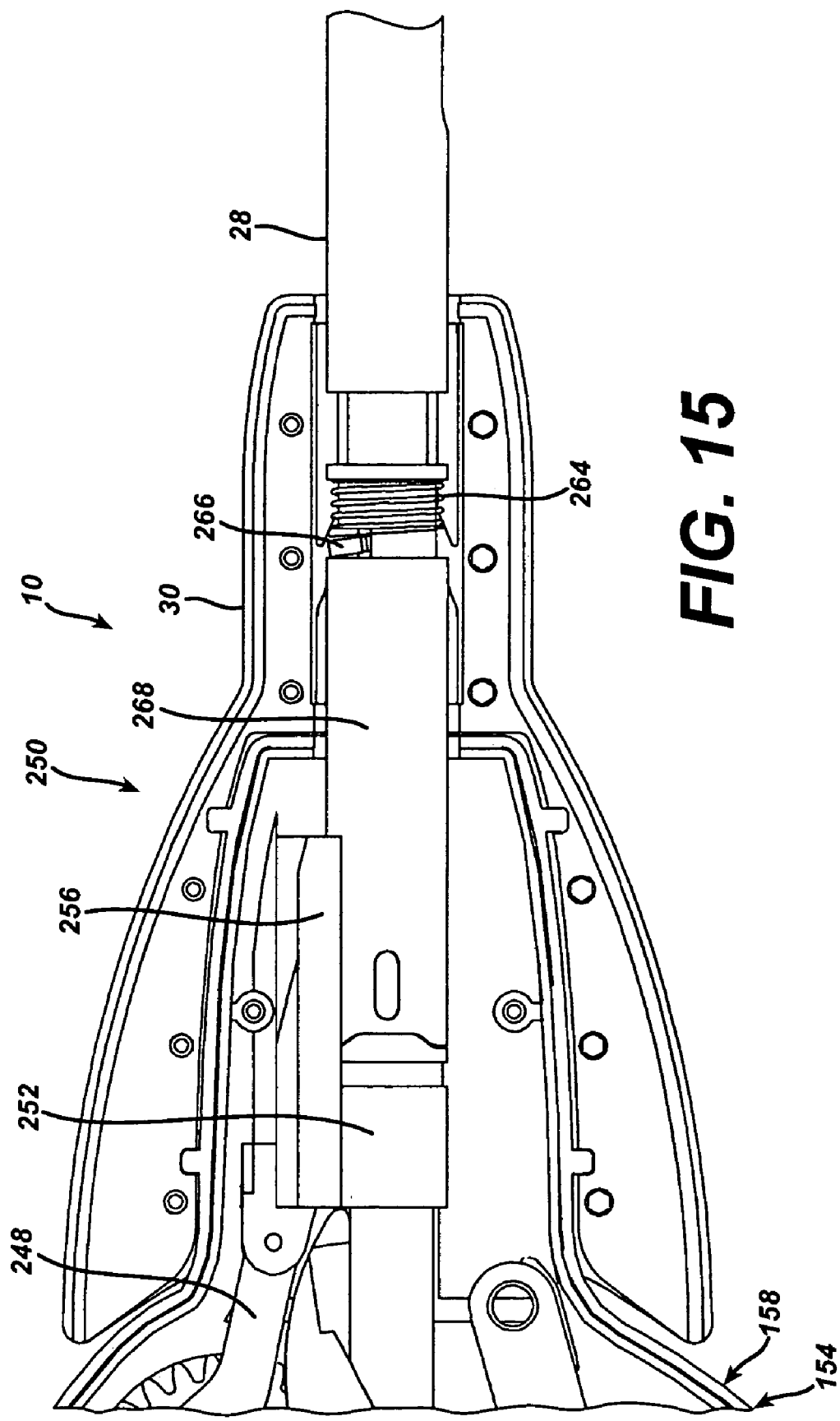
FIG. 15 is a right-side elevation view partially disassembled to expose a distal portion of an anti-backup mechanism in a locked condition in the surgical stapling and severing instrument of FIG. 1.

As described above, the anti-backup mechanism 250 locks during the firing strokes to prevent the firing rod 32 and thus the firing mechanism 150 from retracting until full firing travel is achieved or the user selects to retract. In FIG. 15, the anti-backup mechanism 250 is depicted in a locked condition. The anti-backup release lever 248 is in the proximal-most position and has rotated anti-backup cam slot tube 252 to engage the anti-backup cam tube 268 to form a minimum longitudinal length, creating an increased space for the locking plate 266. Locking plate 266 is tipped to the angle shown by the anti-backup compression spring 264 and grips on the firing rod 32, as shown in FIG. 16.

Figure 16:
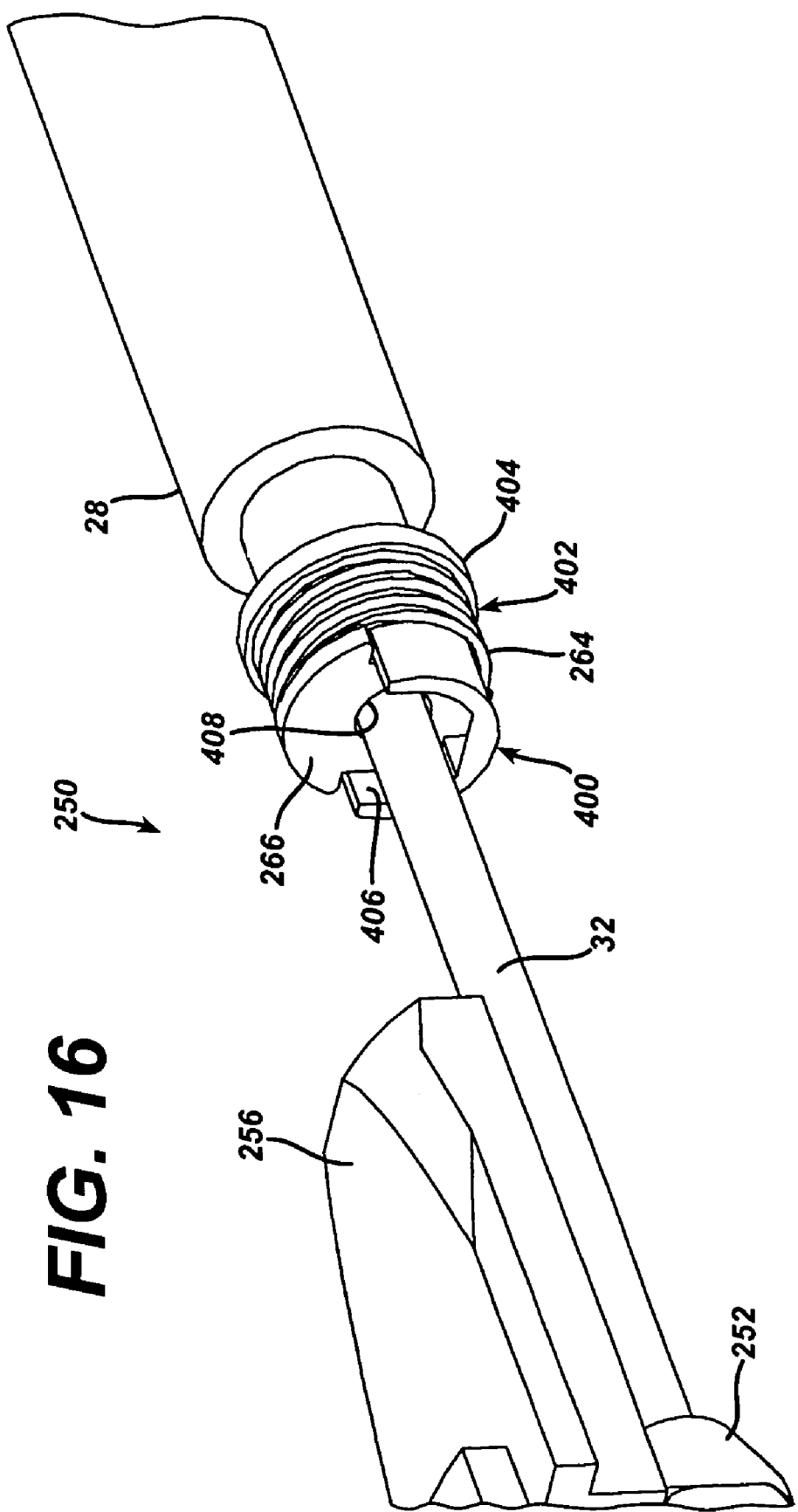
FIG. 16 is a perspective view from a top, aft, right vantage point of the anti-backup mechanism of FIG. 15 with the anti-backup cam tube removed.

In FIG. 16, a proximal end 400 of the frame 28 include a half spool portion 402 that receives the anti-backup compression spring 264 against its distal annular ring 404. Proximal to the spring 264, the frame 28 has a top and proximally open trough 406 that communicates with the interior of the frame 28. The anti-backup plate 266 is a generally flat plate shaped to fit into the open trough 406 adjacent to the spring 264. Central orifice 408 extends through plate 266. In particular, the top portion of the anti-backup plate 266 that is exposed from the open trough 406 projects upwardly to receive a force from the spring 264. The lower portion of the anti-backup plate 266 is longitudinally constrained and not in contact with the spring 264. Thus, unless restrained by the anti-backup cam tube 268, the top of the anti-backup plate 266 is urged to tip proximally, causing the central orifice 408 in the anti-backup plate 266 to bind against the firing rod 32.

Figure 17:
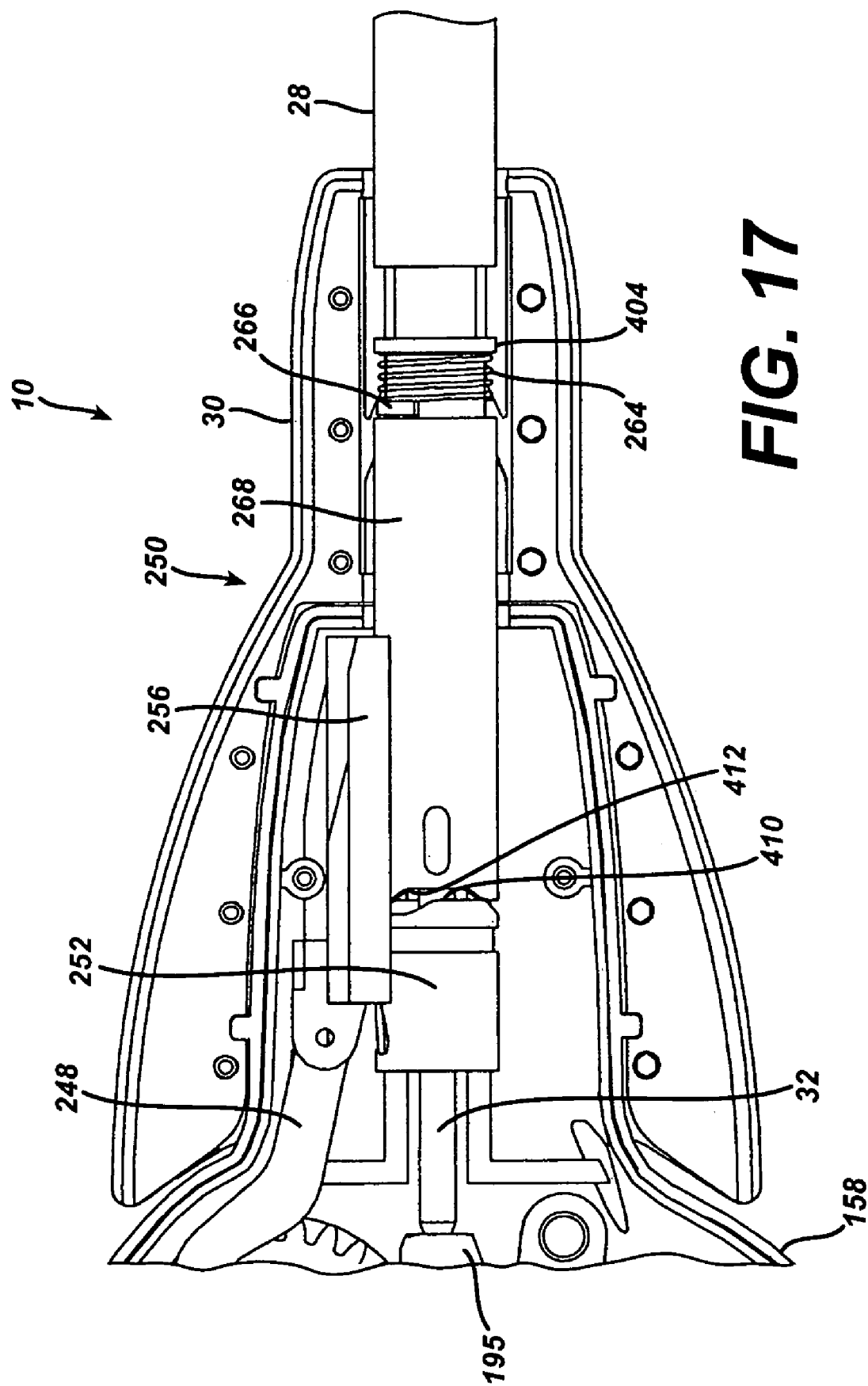
FIG. 17 is a right-side elevation view partially disassembled to expose a distal portion of an anti-backup mechanism in an unlocked condition in the surgical stapling and severing instrument of FIG. 1.

In FIG. 17, the anti-backup mechanism 250 is depicted as unlocked. The anti-lock release lever 248 has laterally moved to the right, impart a movement to the right of the anti-backup yoke 256, thereby imparting a clockwise rotation of the anti-backup cam slot tube 252, when viewed from a proximal position. A camming surface 410 of the anti-backup cam slot tube 252 departs from a proximal cutout 412 in the anti-backup cam tube 268, forcing the latter to move distally against the anti-backup plate 266, which in turn moves to a perpendicular, unlocked position and further compresses anti-backup compression spring 264.

Figure 18:
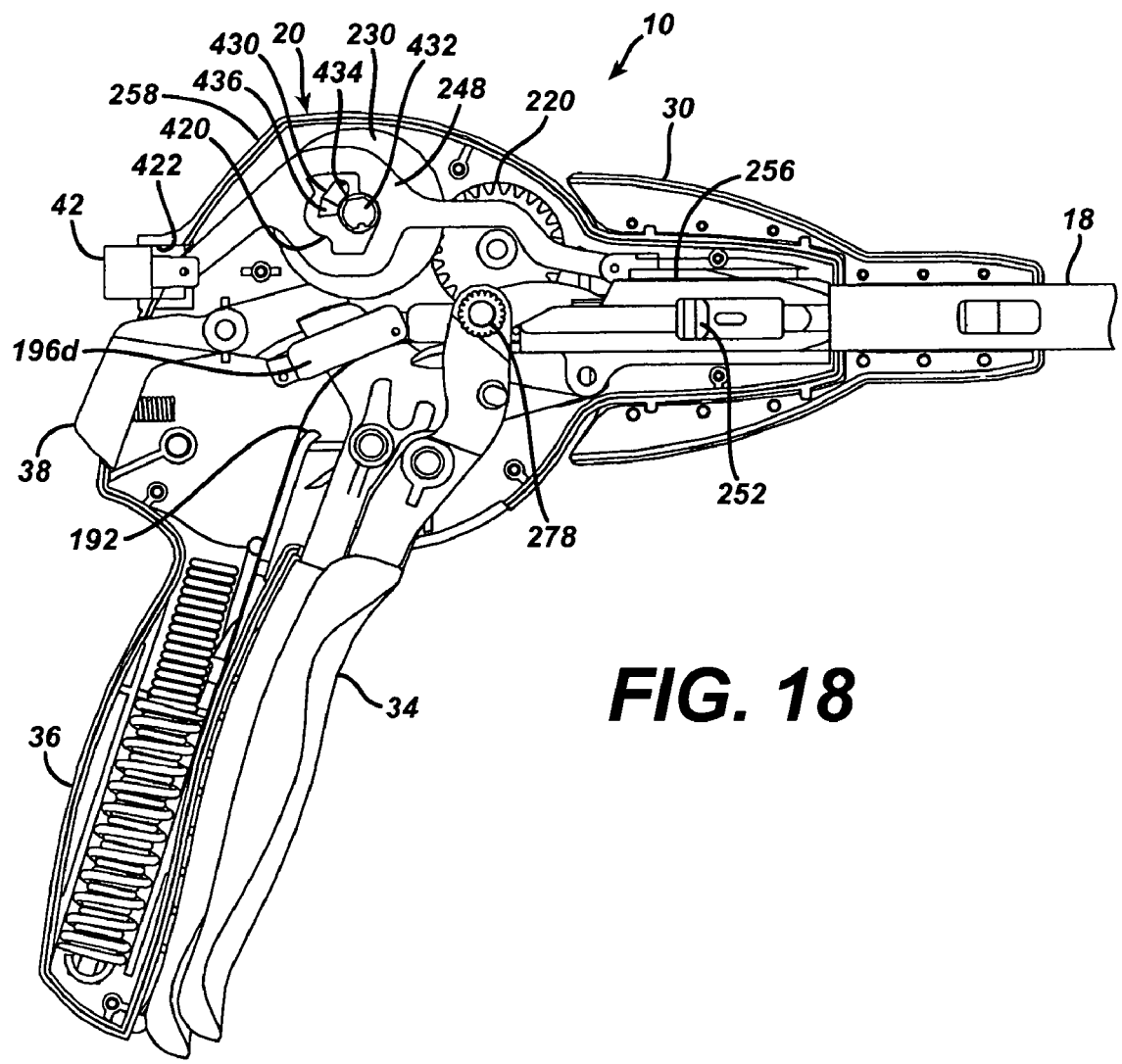
FIG. 18 is a right-side elevation view partially disassembled to expose a distal portion of an anti-backup mechanism in an unlocked condition in the surgical stapling and severing instrument of FIG. 1.

In FIG. 18, the interaction between the anti-backup release lever 248 and the right side of the indicator gear 230 are depicted after the firing trigger 34 has been fired twice. A lever opening 420 extends through anti-backup release lever 248 to receive and interact with a curved ramp 434 extending outwardly from the right side of the indicator gear 230. Rotation of the indicator gear 230 drives the anti-backup release lever 248 distally, which bottoms out the anti-backup release button 42 into a button receptacle 422 and disengages the anti-backup mechanism 250, and proximally, which exposes the anti-backup release button 42 as depicted, as well as kicking the anti-backup release lever 248 to the right to actuate the anti-backup mechanism 250. The anti-backup yoke 256 allows this motion with a longitudinal slotted connection with the anti-backup yoke pin 258 (not shown). These movements of the anti-backup release lever 248 are caused by a curved ramp 430 that surrounds almost a quarter of the circumference of an indicator pin 432, about which the indicator gear 230 turns. The clockwise most portion (when viewed from the right), or peak 434, of the curved ramp 430 projects the farthest to the right away from the surface of the indicator gear 230. The counterclockwise most portion or entry 436 of the curved ramp 430 is thus flush with the surface of the indicator gear 230.

In FIGS. 18-25, the lever opening 420 is shaped with a horizontal slot 440 that defines the proximal and distal movement available to the anti-backup release lever 248, with the indicator pin 432 residing within this horizontal slot 440. A top recess 442 and a bottom recess 444 vertically widen and communicate with the horizontal slot 440 and define at what angular position the clockwise most portion 434 of the curved ramp 430 longitudinally translates the anti-backup release lever 248. The top and bottom recesses 442, 444 are sized to allow the curved ramp 430 to enter the respective recess 442, 444 without tipping the anti-backup release lever 248 until the end of normal firing. The lever opening 420 is above the longitudinal axis of the anti-backup mechanism 250, and thus a rightward force creates a rotating force of the anti-backup cam slot tube 252.

Figure 20:
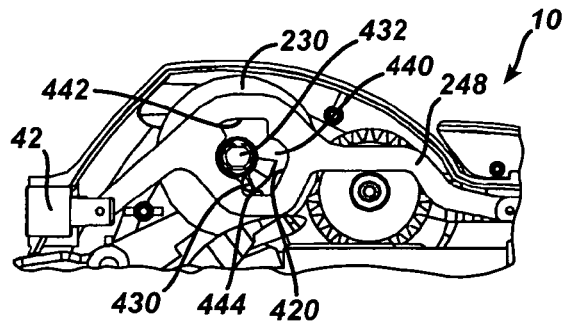
FIGS. 20-25 are detail views of the anti-backup release lever of FIG. 18 depicting respectively a firing sequence of unfired, one firing stroke, two firing strokes, three firing strokes, returning or release button pushed, and fully returned.

In FIG. 20, the anti-backup release lever 248 and indicator gear 230 are shown in their initial condition that remains through the time in which the closure trigger 26 is being actuated. In particular, the anti-backup release lever 248 is distally positioned, bottoming out the anti-backup release button 42 in its button receptacle 422. The curved ramp 430 is at its counterclockwise extreme, with its peak 434 at approximately the 6 o'clock position adjacent distally to a proximal vertical surface of the lower recess 444 of the lever recess 420 with the entry 436 of the ramp 430 at about 3 o'clock.

Figure 19:
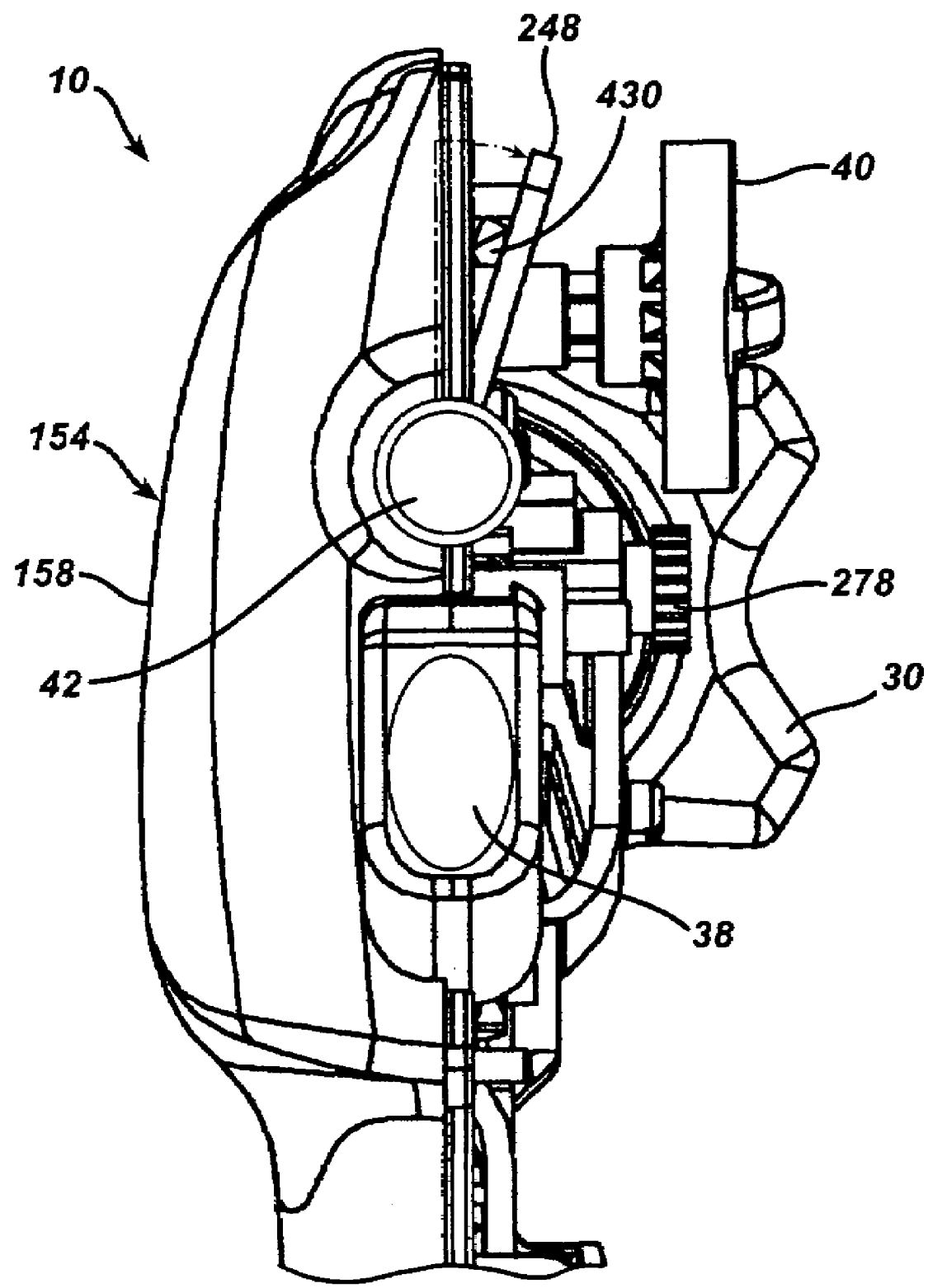
FIG. 19 is a rear elevation view of the surgical stapling and severing instrument of FIG. 1 with the right half shell of the handle housing removed to expose the anti-backup release lever in phantom in a locking condition and in an unlocked condition.
Figure 21:
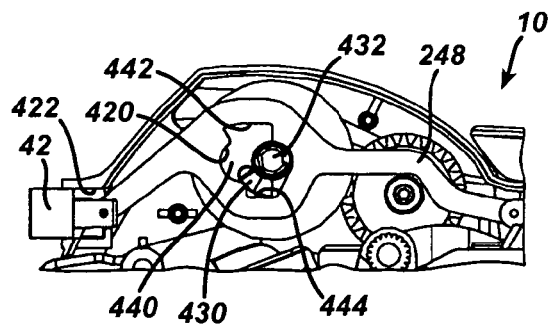
Figure 22:
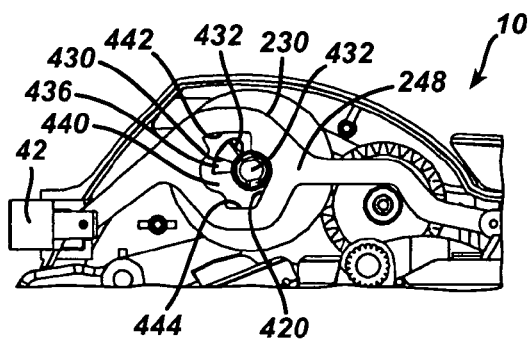

In FIG. 21, the first firing stroke of the firing trigger 34 has occurred, wherein the peak 434 has acted against the proximal vertical surface of the bottom recess 444 and the curved ramp 430 has rotated clockwise to about the 9 o'clock position. Thereby, the anti-backup release lever 248 has translated proximally to exposes the anti-backup release button 42 from the button receptacle 422 and actuated the anti-backup mechanism 250. The relationship of the rate of clockwise rotation of the indicator gear 230 to the desired number of full firing strokes is selected so that the curved ramp 430 continues unimpeded as subsequent firing strokes are made, as depicted in FIG. 22 wherein the two firing strokes have been completed moving the peak to approximately the twelve o'clock position. Thus, the peak 434 is proximal to and adjacent to the distal vertical edge of the upper recess 442, positioned so that a subsequent firing stroke will act upon the anti-backup release lever 248 to cause distal horizontal movement. Note that during these firing strokes that the curved ramp 430 resides proximal to the indicator pin 432. Depressing the release button 42 would cause the proximal edge of the lever opening 420 to ride up onto the curved ramp 430, tilting the anti-backup release lever 248 as depicted in FIG. 19.

Figure 23:
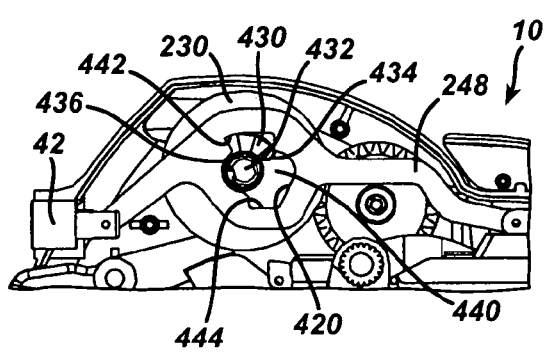

In FIG. 23, the final firing stroke is concluding, during which the peak 434 has moved to approximately 3 o'clock while moving the proximal end of the horizontal slot 440 up against the indicator pin 432, bottoming out the anti-backup release button 42, releasing the anti-backup mechanism 250 and initiating the retraction of linked transmission firing mechanism 150.

Figure 24:
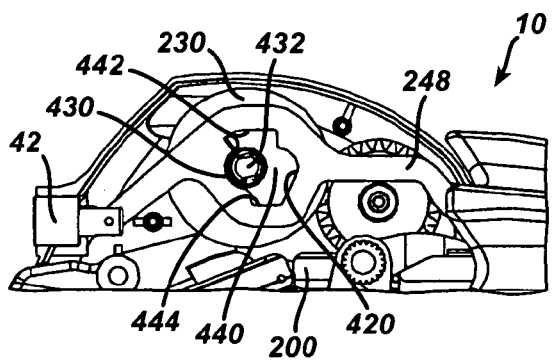
Figure 25:
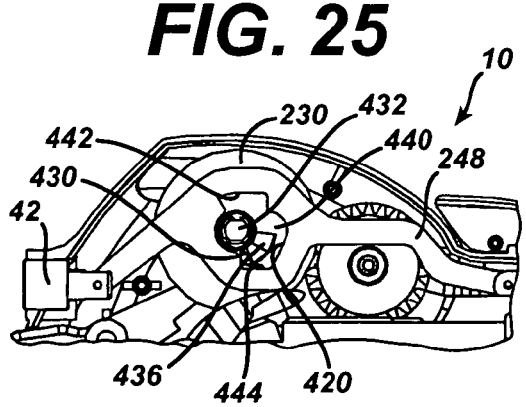

In FIG. 24, the unlocked anti-backup mechanism 250 has allowed the spring-powered retraction of the linked rack 200 to occur, which in turn causes a counterclockwise rotation, when viewed from the right, of the indicator gear 230. As the firing mechanism 150 begins to retract, the counterclockwise rotation of indicator gear 230 slides the angled surface of curved ramp 430 into ramped contact with the proximal edge of the top recess 442. Continued rotation of indicator gear 230 drives the curved ramp 430 under the upper portion of backup release lever 248 and tilts or deflects lever 248 to the position shown in FIG. 19. The tilting motion of the backup release lever 248 is provided to prevent longitudinal motion of lever 248 by the curved ramp 430 during retraction of the linked rack 200. Should the linked rack 200 not retract at the end of the last stroke after anti-backup mechanism 250 is automatically unlocked at the end of the firing sequence, turning the indicator knob 40 (not shown in FIGS. 20-25) would provide extra force to retract the linked rack 200. It should further be appreciated that during partial firing of the firing mechanism 150, such as depicted in FIG. 22, depressing the release button 42 would also retract the linked rack 200 by move the backup release lever 248 distally to unlock the anti-backup mechanism 250. The retraction motion continues until the indicator gear is returned to its initial position, as depicted in FIG. 25.

It should be appreciated that the shape of the lever opening 420 and arcuate size of the arced ramp 430 are illustrative and may be varied to accommodate a handle configured for a different number of firing strokes.

It should be appreciated that the rotary release mechanism formed by the interaction of the indicator gear 230 and the lever opening 420 may be replaced with other linkages.

Opening Lockout.

Figure 26:
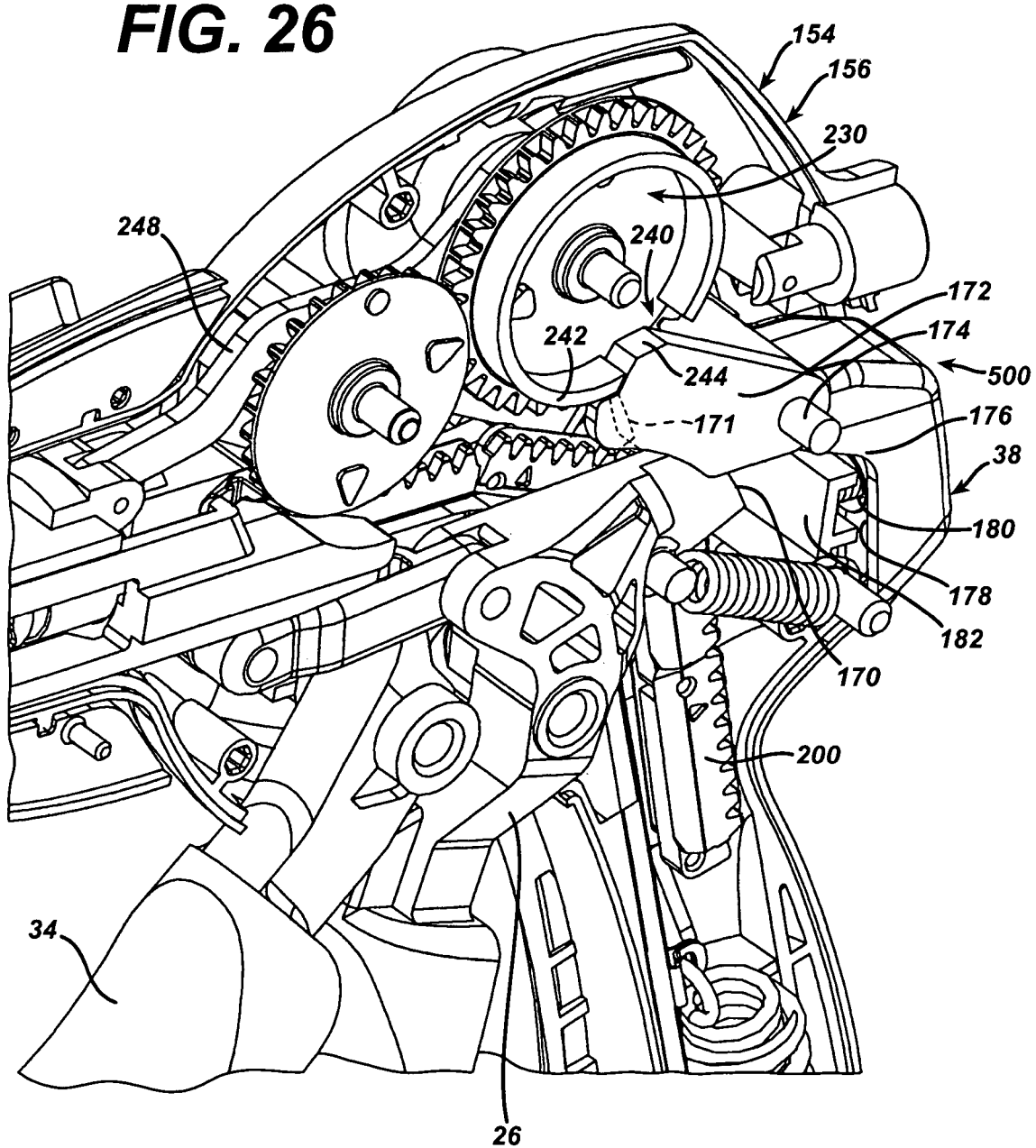
FIGS. 26-27 are perspective view from a top, left, distal vantage point of the surgical stapling and severing instrument with the right half shell of the handle housing removed to expose a closure release lockout mechanism, respectively in an initial position with lockout removed and closure release button depressed, and then a lockout being activated during initial firing.
Figure 27:
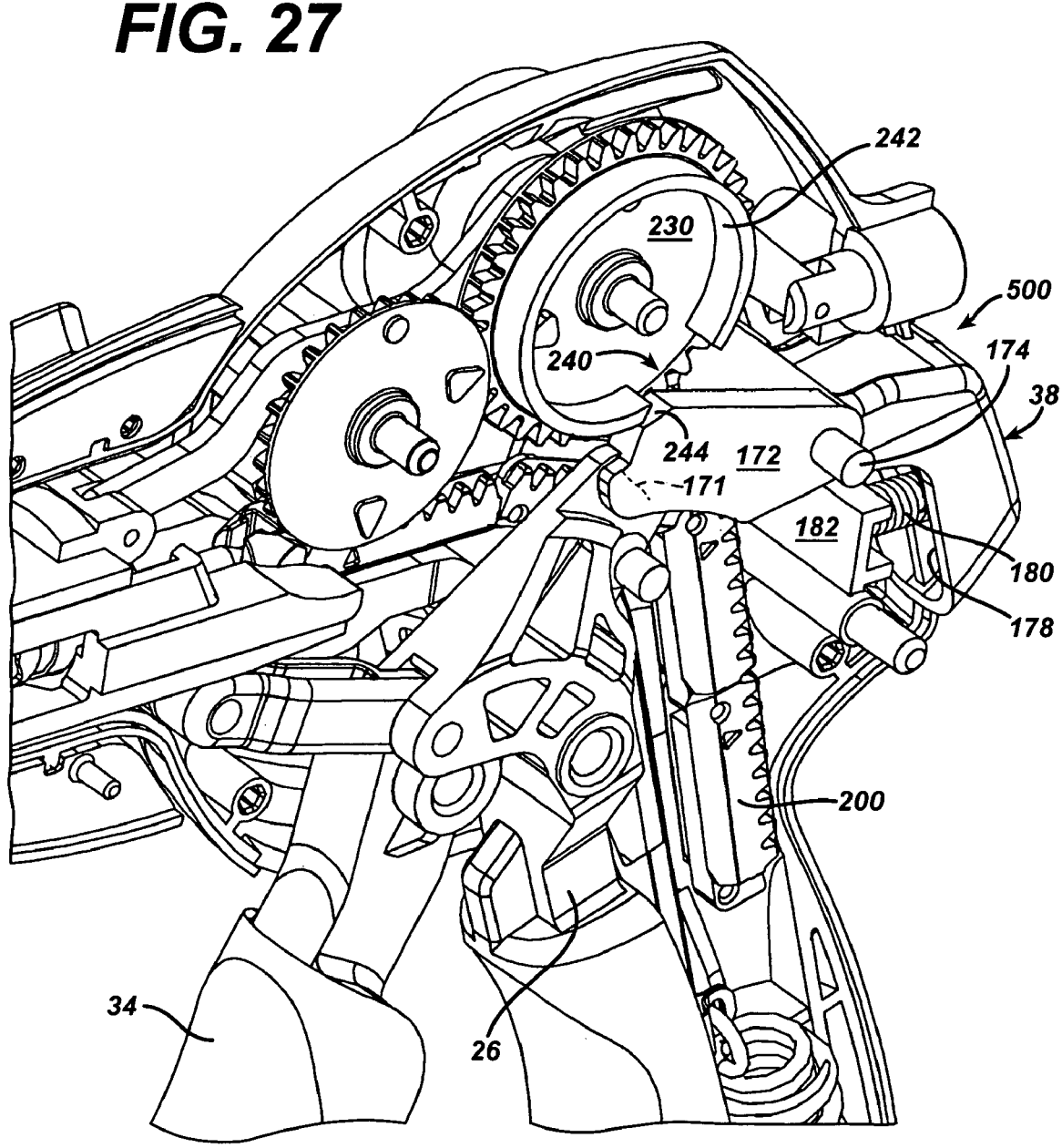

In FIG. 26, the surgical stapling and severing instrument 10 is in its initial open condition with both closure and firing triggers 26, 34 forward and the linked rack 200 retracted. As described above, in this unfired condition, the indicator gear 230 presents its opening 240 in circular ridge 242 to the upper surface 244 of the locking arm 172, which is ordinarily rotated downward out of the opening 240 by the action of the compression spring 180 between the housing structure 182 and the intermediate distal side 178 of the closure release button 38. In FIG. 26, the closure release button 38 has been depressed, causing the upper surface 244 into the opening 240. In FIG. 27, the closure trigger 26 and the locking arm 172 are in clamping abutment after closing with the closure trigger 26 against the pistol grip 36 and the firing trigger 34 swung into position for firing. The closure release button 38 is not depressed, as noted by the expanded closure spring 180. The upper surface 244 of the locking arm 172 is swung below circular ridge 242 and indicator gear 230 is unlocked and free to rotate counterclockwise. The downward movement of locking arm 172 unlocks the indicator gear 230 and connected linked transmission firing mechanism 150 and allows the firing trigger 34 to be actuated. Thus, as the indicator gear 230 continues to rotate with further firing, the closure release button 38 is precluded from releasing the clamped closure trigger 26.

Position Indicator and Release Mechanism.

Figure 28:
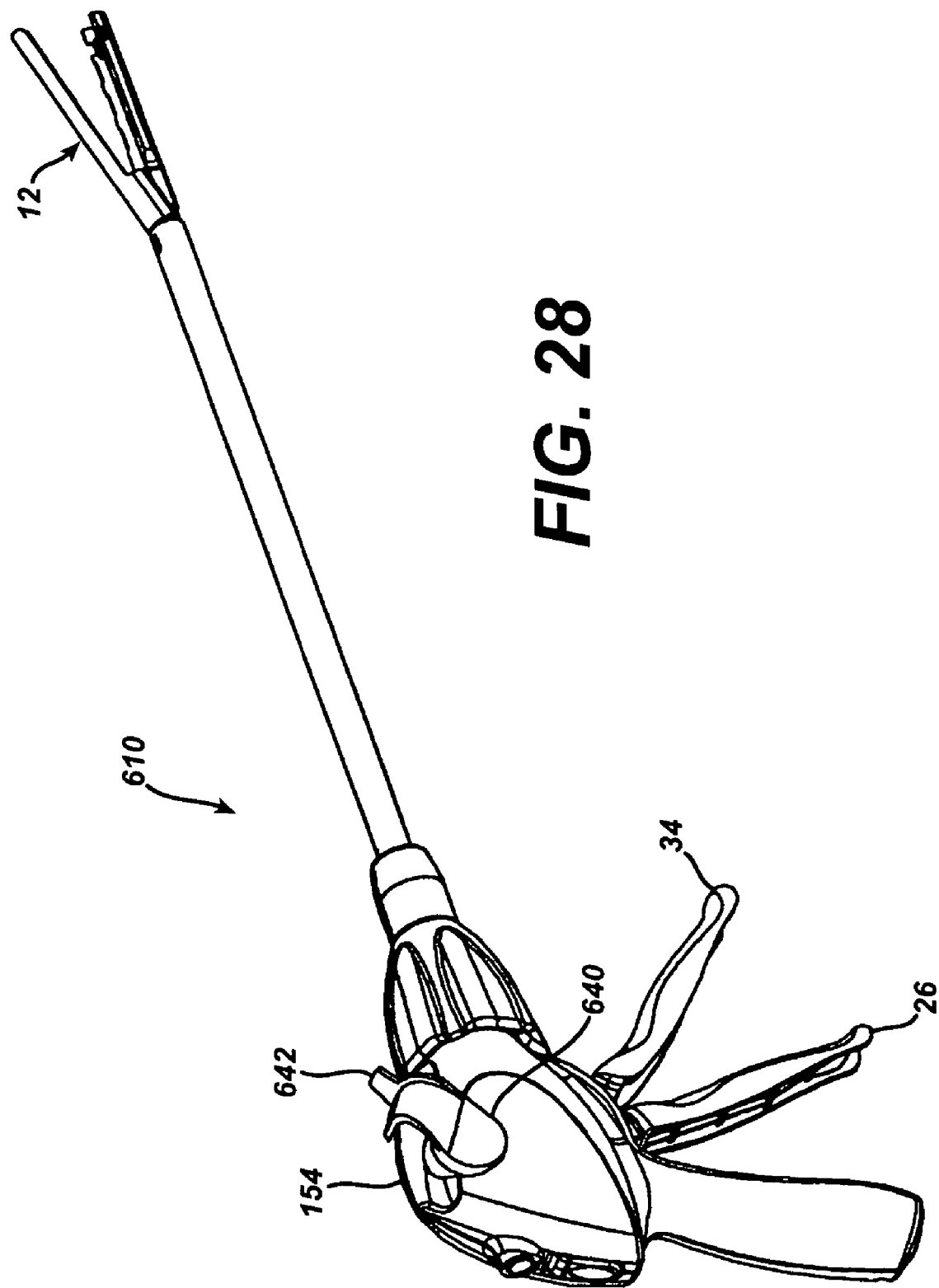
FIG. 28 is perspective view of a surgical stapling and severing instrument in an open condition similar to FIG. 1 but incorporating a top-accessible retraction lever.

In FIG. 28, a surgical stapling and severing instrument 610 has the indicator retraction knob replaced by an alternate indicator device 640 upwardly extended to present a top-accessible retraction lever 642 that functions as a stuck firing retractor that may be readily actuated by either hand. The instrument is shown opened and unfired, as indicated by the distally forward closure and firing triggers 26, 34 and the open end effector 12. When firing has not commenced, the retraction lever 642 is normally distally rotated adjacent to the handle housing 154. The indicator 640 may be coupled (not shown) to the previously described idler gear 220 and a firing mechanism 150 as described previously in which the retraction lever 642 would rotate proximally as the linked transmission is fired, presenting a visual indication of firing as well as allowing a way of assisting automatic retraction by applying a manual distal force thereto as a rotary position indicator, the direction of rotation must be reversed so it must be attached to the idler gear 220 for this embodiment.

Figure 29:
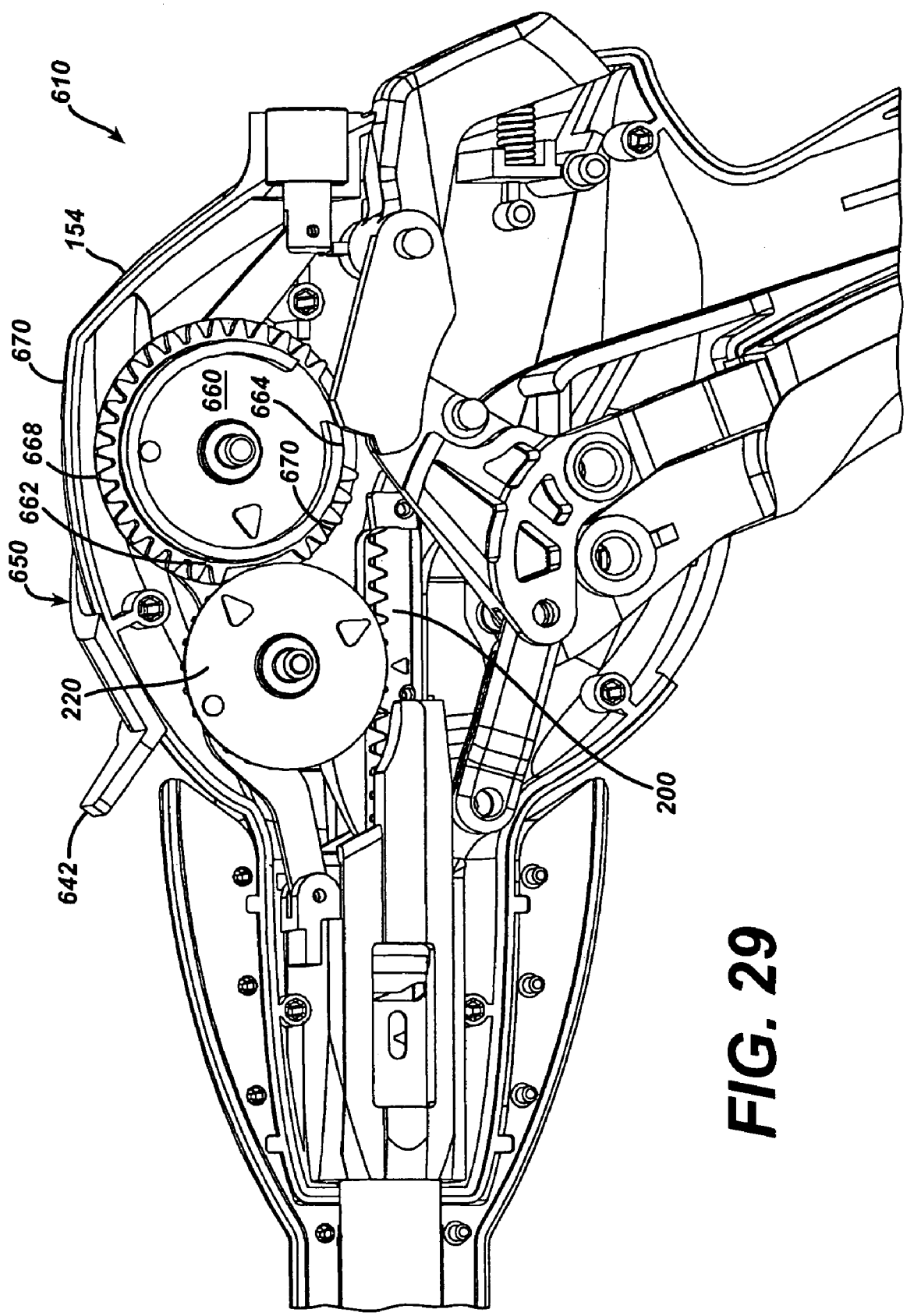
FIG. 29 is a left side elevation view of the surgical stapling and severing instrument of FIG. 28 with the left half shell of the handle housing removed to expose an intermittently toothed indicator gear presenting a first dwell area to the idler gear.

In FIG. 29, another alternate firing mechanism 650 incorporates the afore-described top-accessible retraction lever 642 and indicator device 640 that is coupled to an indicator gear 660 having first and second dwell areas 662, 664 within a toothed area 668. The first dwell area 662 is presented to the idler gear 220 when the retraction lever 642 is at its distal position adjacent to the handle housing 154. Thereby, the idler gear 220 is allowed free clockwise and counterclockwise rotation as driven by the longitudinally moving linked rack 200. Should the E-beam 80 (not shown in FIG. 29) become stuck within the end effector 12 for any reason and cannot be withdrawn proximally by the combination tension/compression spring 184, the retraction lever 642 may be pulled proximally by the surgeon to rotate the indicator gear 660 clockwise, as viewed from the left. This rotational movement of the retraction lever 660 rotates the indicator gear 660 and brings a curved tooth segment 670 that is between the first and second dwell 662, 664 into contact with the teeth of the idler gear 220 to operably couple the retraction lever 642 to the firing mechanism 650.

Figure 30:
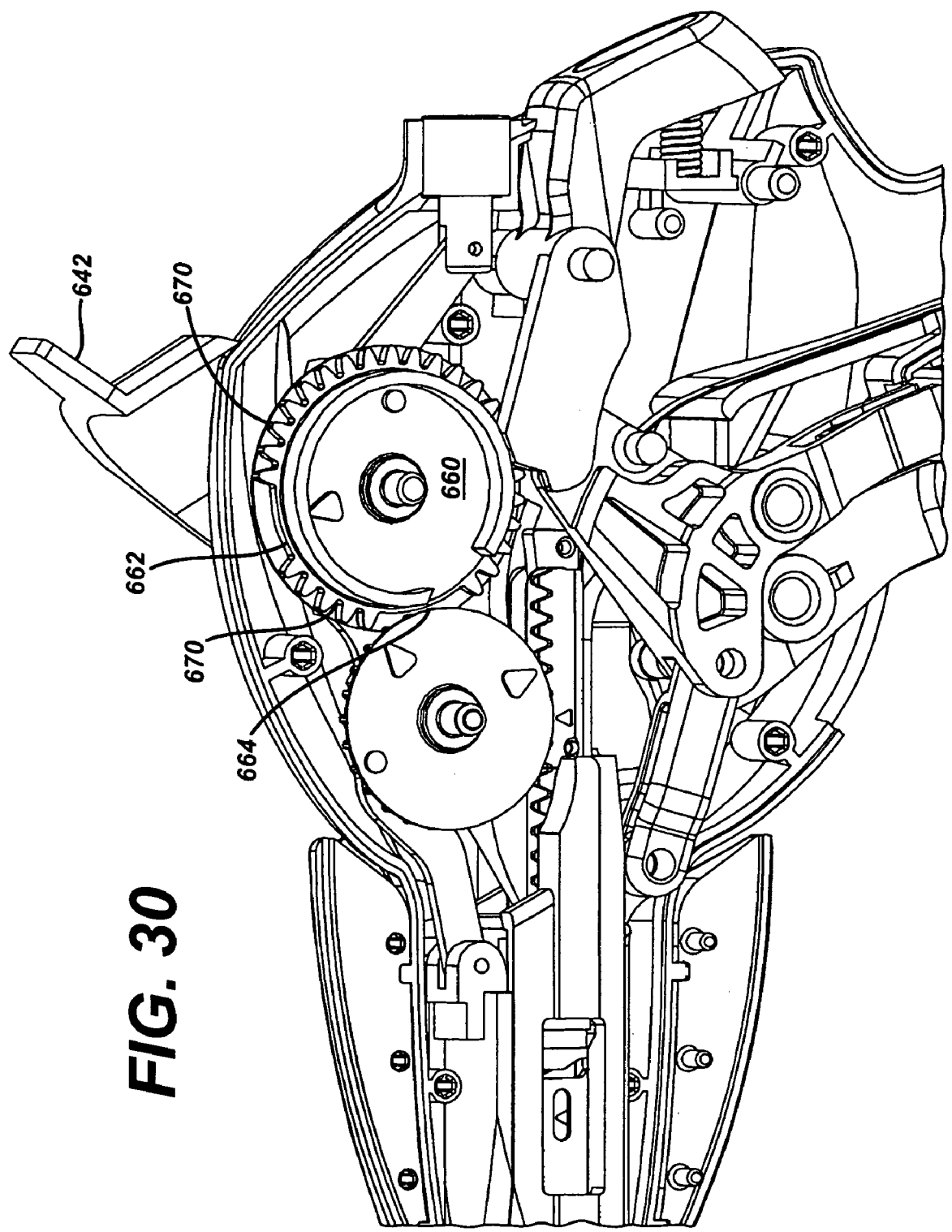
FIG. 30 is a left side elevation view of the surgical stapling and severing instrument of FIG. 28 with the left half shell of the handle housing removed to expose an intermittently toothed indicator gear presenting a second dwell area to the idler gear.

Once coupled, the surgeon may apply extra force to the retraction lever 642 to retract the firing mechanism 650, thereby rotating the idler gear 220 counterclockwise and longitudinally moving the linked rack 200 proximally to retract the E-beam 80. As the retraction lever 642 is further rotated to the position of FIG. 30, the idler gear 220 disengages with the curved tooth segment 670 and is decoupled from the retraction lever 642 by second dwell area 664. At this point, the application of force has freed the stuck firing mechanism 650 and the combination tension/compression springs 184 will fully retract the linked rack 200.

An alternate design (not shown) involves the addition of a one way slip clutch such as a Sprague clutch or an equivalent (not shown) between the retraction lever 642 and the indicator gear 660. In the previous design, the range of motion of the retraction lever 642 is limited by contact with the handle housing 154 at each end of the range or motion less than a full revolution. This limits the distance that the firing system 650 can be retracted for one movement of the retraction lever 642. The addition of the one way slip clutch between the retraction lever 642 and indicator gear 660 allows the retraction lever 642 to operably engage with the indicator gear 660 as the retraction lever 642 rotates back (distal to proximal) and disengages as the lever moves forward (proximal to distal). This ensures full retraction of the firing mechanism 650 by allowing multiple pulls on the retraction lever 642. Second dwell area 664 may be removed from the indicator gear 660 to ensure more tooth to tooth engagement. Additionally, the incorporation of a clutch mechanism allows the retraction lever to be rotated adjacent to the handle after use.

In use, the surgeon positions the end effector 12 and shaft 18 through the cannula or a trocar to a surgical site, positioned the anvil 14 and elongate channel 16 as opposing jaws to grasp tissue to be stapled and severed. Once satisfied with the position of end effector 12, the closure trigger 26 is full depressed toward the pistol grip 36 of the handle 20, causing the upper portion 160 of the closure trigger 26 to lock against a locking arm 172 that is pivotally attached to the closure release button 38. Then, the firing trigger 34 is depressed and released a predetermined number of times to effect full firing travel to drive a firing rod 32 down the shaft 18 to the E-beam 80 in the end effector 12. During firing, the anti-backup mechanism 250 is in a locked condition, with an anti-backup plate 266 allowed to tip back, binding any proximal motion of the firing rod 32. The distal firing motion is imparted to the firing rod 32 by a linked transmission firing mechanism 150 that includes linked rack 200 proximally attached to the firing rod 32, with each link 196a-d pinned to adjacent links 196a-d such that bending is allowed down into the pistol grip 36 but not upward, forming a rigid structure when straight with a force imparted above the pivot pins 310 between links 196a-d. Specifically, a traction biasing mechanism 210 coupled to the firing trigger 34 includes a biasing wheel 278 that is frictionally coupled the handle housing 154 such that a distal firing motion imparts an engaging bias to the pawl 270, urging the pawl 270 into engagement with the linked rack 200. At the end of the stroke, the pawl 270 is lifted from firing engagement with link 196 by being brought into contact with angled surface 284 of the closure yoke 162. A return motion of the firing mechanism 150 causes the biasing wheel 278 to impart a reversing bias to the pawl 270, holding pawl 270 above the linked rack 200 that is thereby held in place by the anti-backup mechanism 250. Upon full firing travel, the indicator gear 230 includes the curved ramp 430 that trips the anti-backup release lever 248 that forces the anti-backup plate 266 into an unlocked condition, allowing the linked rack 200, and thus the firing rod 32, to be withdrawn by a compressive force stored in a combination tension/compression spring 184. Thereby, the linked rack 200 is withdrawn into the handle grip 36. Alternatively, during the firing strokes, the surgeon may depress the anti-backup release button 42 that causes the anti-backup release lever to tip. The indicator knob 40 may advantageously allow the surgeon to know how far firing has progressed and to assist in retracting the E-beam 80 that has encountered binding.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For instance, while a surgical stapling and severing instrument 10 is described herein that advantageously has separate and distinct closing and firing actuation, providing clinical flexibility. However, it should be appreciated that applications consistent with the present invention may include a handle that converts a single user actuation into a firing motion that closes and fires the instrument.

What is claimed is:

1. A surgical instrument, comprising:
   an elongate implement portion responsive to a firing motion and a closure motion;
   a firing mechanism operably configured to produce the firing motion between an unfired position and a fully fired position to eject a staple from a staple cartridge into tissue;
   a closing mechanism operably configured to close and to open the implement portion;
   a closing release mechanism operably configured to lock the closing mechanism when the implement portion is in the fully closed position, and responsive to an operator command to unlock the closing mechanism when the firing mechanism is in an unfired position; and
   a lockout mechanism operably configured to lock the closing release mechanism when:
      (i) the implement portion is in the fully closed position, and
      (ii) the firing mechanism is in any position other than the unfired position.

2. The surgical instrument of claim 1, wherein the implement portion comprises:
   an elongate channel connected to the shaft,
   an anvil pivotally coupled to the elongate channel for clamping tissue, and
   the staple cartridge received in the elongate channel;
   wherein the firing mechanism further comprises a firing member, wherein the firing member distally terminates in a firing bar operably configured to actuate the staple cartridge to form staples in the clamped tissue.

3. The surgical instrument of claim 1, wherein the firing mechanism further comprises a firing member, wherein the firing mechanism is further operably configured to transfer sequential firing strokes into distal longitudinal movement of the firing member.

4. The surgical instrument of claim 1, wherein the firing mechanism further comprises a firing trigger having a means for traction biasing, wherein the means for traction biasing couples multiple firing trigger actuations by an operator to produce a firing motion.

5. The surgical instrument of claim 1, wherein the firing mechanism further comprises a firing member and a linked rack operably coupled to a firing trigger to transmit firing trigger actuations by an operator to the firing member.

6. The surgical instrument of claim 5, wherein the firing mechanism further comprises a means for traction biasing to couple multiple firing trigger actuations by an operator to the linked rack.

7. A surgical instrument, comprising:
   an elongate implement portion responsive to a firing motion and a closure motion;
   a firing mechanism operably configured to produce the firing motion between an unfired position and a fully fired position, wherein when the firing mechanism moves from the unfired position to the fired position, at least one staple is ejected from a cartridge and into tissue;
   a closing mechanism operably configured to close and to open the implement portion;
   a closing release means to clamp the implement portion in the fully closed position, and responsive to an operator command to open the implement portion when the firing mechanism is in an unfired position; and
   a lockout mechanism configured to lock the clamped implement portion in the fully closed position when the firing mechanism is in any position other than the unfired position.

* * * * *